US008109946B2

(12) United States Patent
Cahill et al.

(10) Patent No.: US 8,109,946 B2
(45) Date of Patent: Feb. 7, 2012

(54) ADJUSTABLE LENGTH PATENT FORAMEN OVALE (PFO) OCCLUDER AND CATCH SYSTEM

(75) Inventors: Ryan Cahill, Brighton, MA (US); John Ahern, Boston, MA (US); Timothy J. Fallon, Melrose, MA (US); Steven W. Opolski, Carlisle, MA (US); David J. Callaghan, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 658 days.

(21) Appl. No.: 11/729,636

(22) Filed: Mar. 29, 2007

(65) Prior Publication Data

US 2007/0250081 A1    Oct. 25, 2007

Related U.S. Application Data

(60) Provisional application No. 60/787,989, filed on Mar. 31, 2006, provisional application No. 60/817,393, filed on Jun. 30, 2006.

(51) Int. Cl.
*A61B 17/08* (2006.01)

(52) U.S. Cl. ............................................. 606/151

(58) Field of Classification Search ............... 623/23.72; 606/213, 151, 157, 158, 232; 411/340–342; 24/102 A, 102 E, 453
See application file for complete search history.

(56) References Cited

U.S. PATENT DOCUMENTS

| 6,548,569 B1 | 4/2003 | Williams et al. |
| 6,610,764 B1 | 8/2003 | Martin et al. |
| 2003/0181945 A1 | 9/2003 | Opolski et al. |
| 2004/0220610 A1* | 11/2004 | Kreidler et al. ............... 606/200 |
| 2005/0043759 A1* | 2/2005 | Chanduszko ................. 606/213 |
| 2005/0053416 A1 | 3/2005 | Kwan |
| 2005/0234509 A1* | 10/2005 | Widomski et al. ............ 606/213 |
| 2005/0267523 A1* | 12/2005 | Devellian et al. ............. 606/213 |
| 2005/0273135 A1* | 12/2005 | Chanduszko et al. ........ 606/213 |

(Continued)

FOREIGN PATENT DOCUMENTS

WO    WO-03/032818 A2    4/2003

(Continued)

OTHER PUBLICATIONS

International Search Report, International Application No. PCT/US2007/065536, mailed Jul. 27, 2007. (2 Pages).

(Continued)

*Primary Examiner* — Melanie Tyson
*Assistant Examiner* — Son Dang
(74) *Attorney, Agent, or Firm* — DLA Piper LLP (US)

(57) ABSTRACT

Devices, delivery systems and techniques for an occlusion device for the closure of physical anomalies, such as an atrial septal defect, a patent foramen ovale (PFO), and other septal and vascular defects are described. The devices, delivery systems and techniques relate to, but are not limited to, a patent foramen ovale (PFO) occluder made from a substantially cylindrical form. An occluder having a distal side and a proximal side, with a catch system for securing the deployed configuration, is introduced into the treatment site by a delivery sheath. In one aspect, the occluder has an adjustable length center joint that allows the device to fit a particular septal defect. In some embodiments, the occluder includes a catch member that holds the occluder in the deployed, expanded profile configuration. In one aspect, the catch member also has an adjustable length.

35 Claims, 14 Drawing Sheets

U.S. PATENT DOCUMENTS

| | | |
|---|---|---|
| 2006/0052821 A1* | 3/2006 | Abbott et al. .................. 606/213 |
| 2006/0122647 A1 | 6/2006 | Callaghan et al. |
| 2006/0265004 A1* | 11/2006 | Callaghan et al. ............ 606/213 |
| 2007/0010851 A1 | 1/2007 | Chanduszko et al. |
| 2007/0073337 A1* | 3/2007 | Abbott et al. .................. 606/213 |
| 2007/0129755 A1* | 6/2007 | Abbott et al. .................. 606/213 |
| 2007/0167981 A1 | 7/2007 | Opolski et al. |

FOREIGN PATENT DOCUMENTS

| | | |
|---|---|---|
| WO | WO-2006/028813 A2 | 3/2006 |

OTHER PUBLICATIONS

U.S. Appl. No. 11/728,694, Callaghan.

U.S. Appl. No. 60/787,988, Callaghan.

U.S. Appl. No. 60/847,703, Cahill.

* cited by examiner

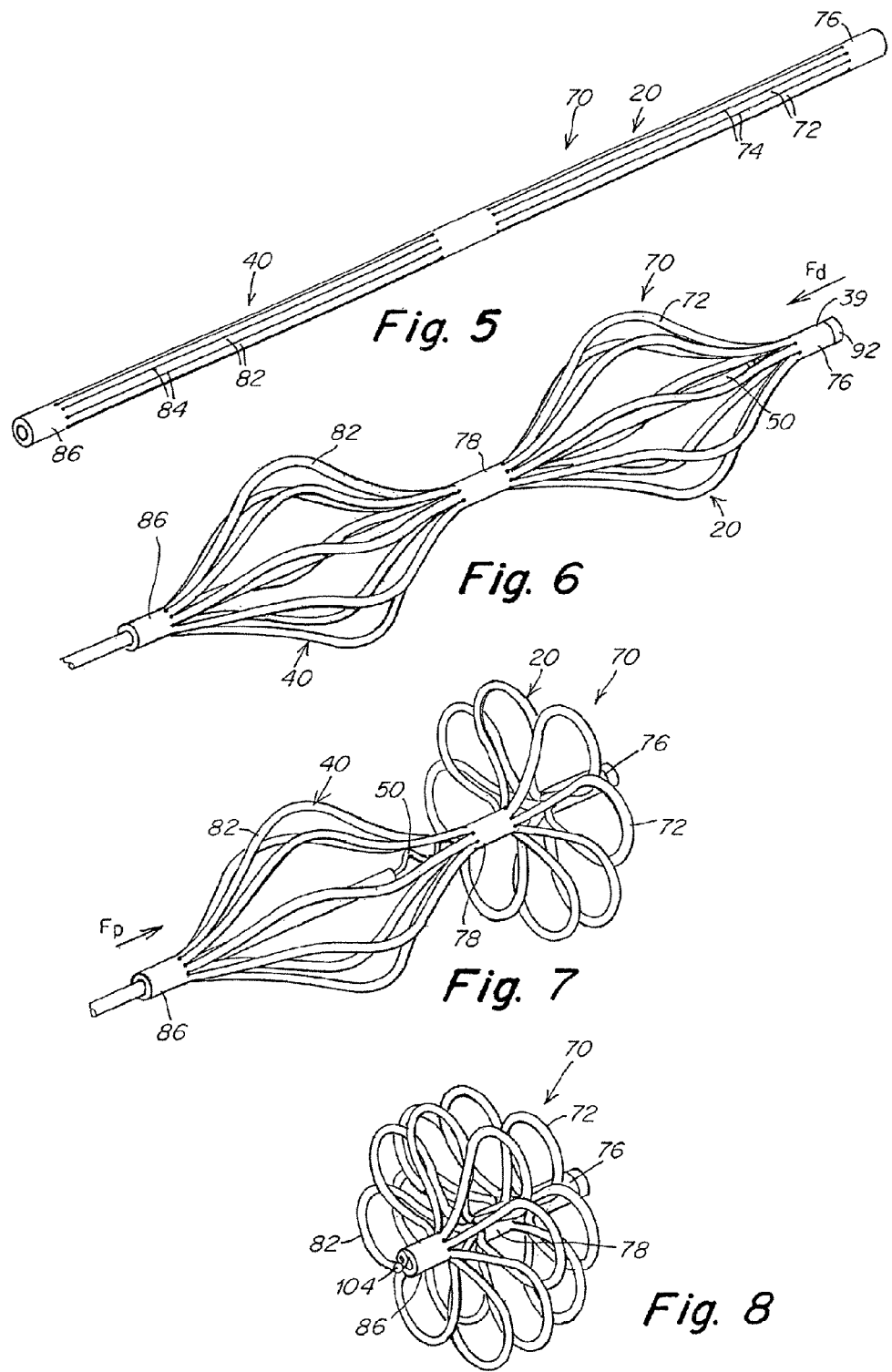

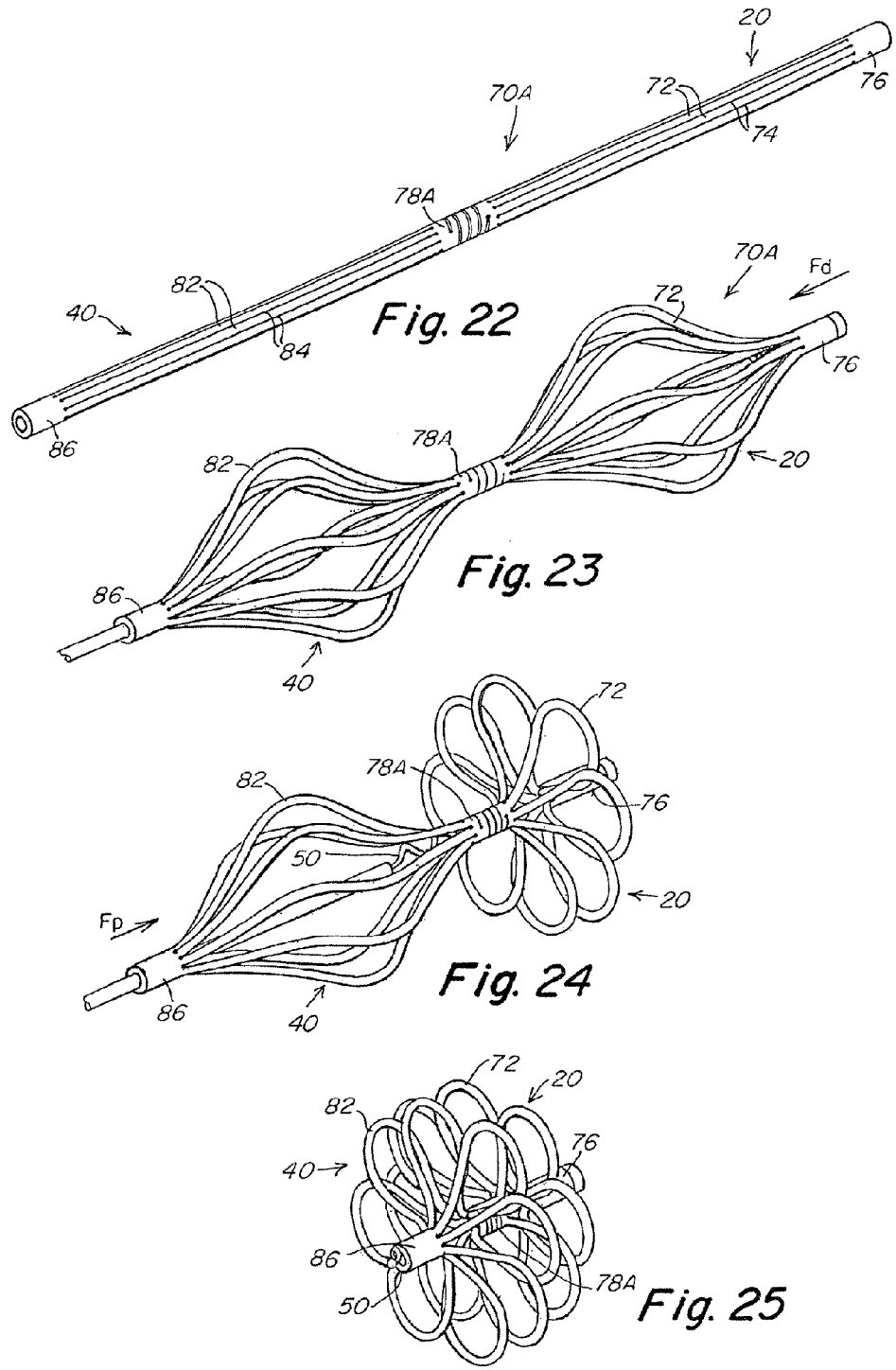

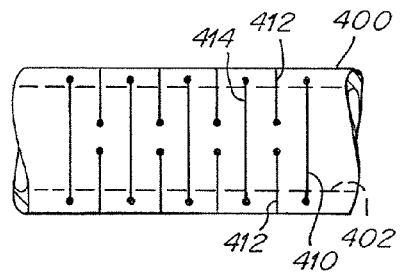
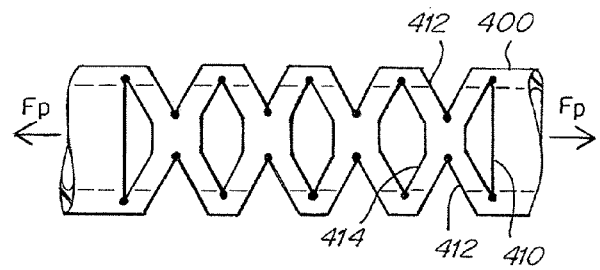
Fig. 29A          Fig. 29B
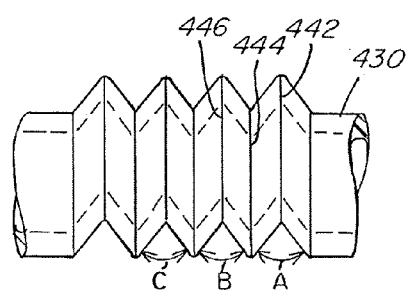
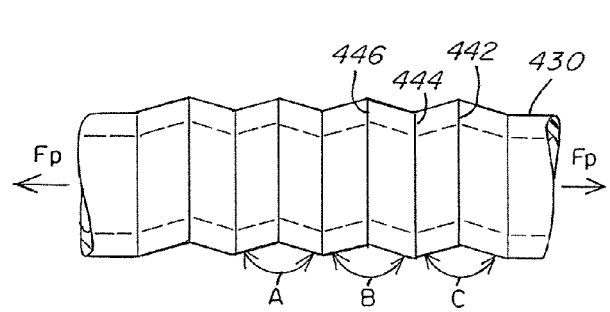
Fig. 30A          Fig. 30B
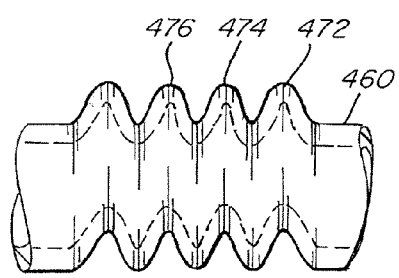
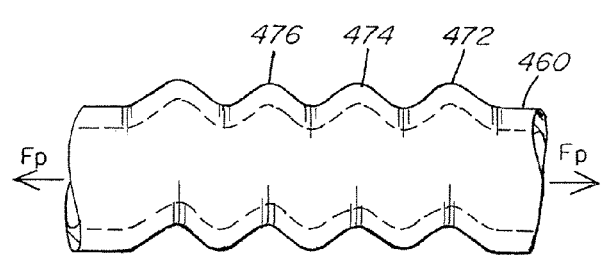
Fig. 31A          Fig. 31B

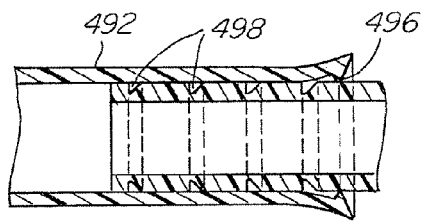
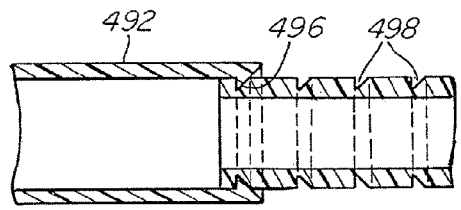
Fig. 32A　　　　　　　Fig. 32B
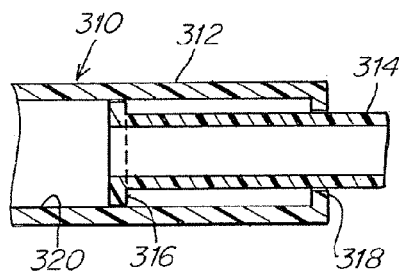
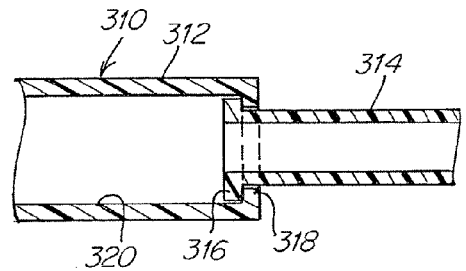
Fig. 33A　　　　　　　Fig. 33B
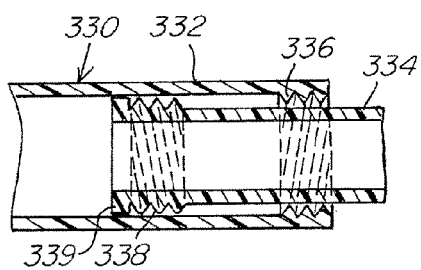
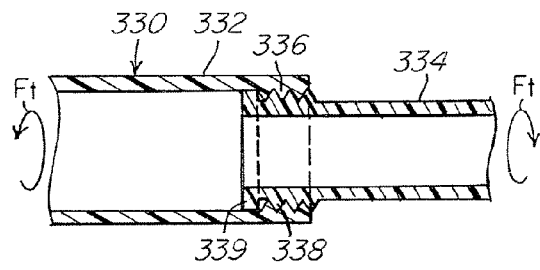
Fig. 34A　　　　　　　Fig. 34B

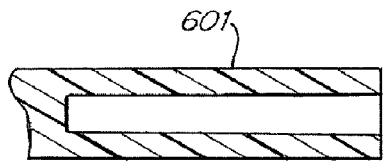
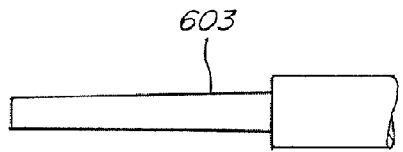
Fig. 38A    Fig. 38B
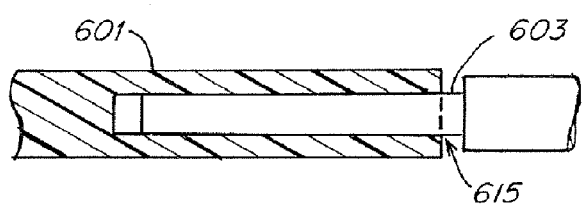
Fig. 39A
Fig. 39B
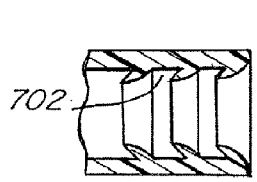
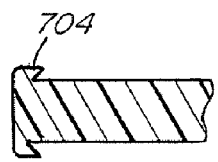
Fig. 40A    Fig. 40B
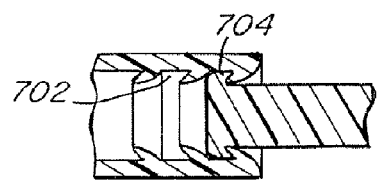
Fig. 41

ADJUSTABLE LENGTH PATENT FORAMEN OVALE (PFO) OCCLUDER AND CATCH SYSTEM

CROSS-REFERENCE TO RELATED APPLICATIONS

This application claims the benefit under 35 U.S.C. 119(e) of U.S. Provisional Application No. 60/787,989, filed on Mar. 31, 2006, which is incorporated by reference herein in its entirety.

This application also claims the benefit under 35 U.S.C. 119(e) of U.S. Provisional Application No. 60/817,393, filed on Jun. 30, 2006, which is incorporated by reference herein in its entirety.

FIELD OF THE INVENTION

This invention relates generally to occlusion devices for the closure of physical anomalies, such as an atrial septal defect, a patent foramen ovale (PFO), and other septal and vascular defects. In particular, the invention relates to occlusion devices with an adjustable length center joint. The invention also relates to catch systems and delivery systems and techniques for such devices.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. The presence of a PFO has also recently been linked to chronic migraines. While the reasons are still under investigation, PFO closure has been shown to eliminate or significantly reduce chronic migraine headaches in many patients.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various devices and delivery systems have been developed to deliver occluders and other medical devices through body lumens. Some delivery systems of the prior art are used to deliver devices that readily expand to a delivered configuration when removed from the delivery system. Other occluders do not readily expand into a deployed configuration and techniques are used to change the configuration of the device into the deployed configuration. In the latter case, once an occluder is delivered to the desired delivery site and deployed, the occluder must have a catch system that keeps the device in the deployed configuration.

The devices and techniques disclosed herein are designed to address these and other deficiencies of prior art septal closure devices and techniques for delivering and retrieving such devices.

SUMMARY OF THE INVENTION

Aspects of the invention relate to implants including an occluder and a catch system for the occluder, as well as devices and techniques for delivering an implant into a desired location within the body and securing the implant in the deployed configuration. In certain embodiments, the implants include, but are not limited to, a septal occluder made from a polymer tube or a tubular form defined by filaments having delivery and deployment configurations.

These delivery techniques, in addition to use with septal occluders, could be applied to other medical devices, such as other expandable devices constructed from an underlying tubular structure.

Certain embodiments of the present invention further include a catch system for securing an occluder in a deployed configuration. In some embodiments, the catch system includes a catch member, preferably disposed in an axially central portion of a septal occluder. Catch members are constructed and arranged to apply force of desired magnitude and orientation to designated portions of the occluder device to maintain the occluder at its implant location. In preferred embodiments, the catch member is adjustable along at least its axial length, enabling occluder implantation in and closure of PFO's having a variety of dimensions.

Aspects of the present invention relate to devices and techniques for making the center joint of the occluder expandable so that an occluder can accommodate different thicknesses of septal tissue. In one embodiment, a helical cut is provided in the center joint and it expands as needed in the desired delivery location. An expandable catch member may be used in this configuration also.

In another embodiment of the invention, the center joint is constructed of coil, braid or zig-zag construction. In still another embodiment, the center joint may be a telescoping system.

According to at least some embodiments, the occluder is substantially tubular or cylindrical. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the device is formed by cutting the tube. In other embodiments, the occluder is formed by aligning and selectively bonding a plurality of filaments in a substantially cylindrical shape. The occluder is placed in its deployment configuration by reducing the axial length of the device.

In another aspect, the present invention provides a catch system that includes a catch member that has an adjustable catch distance, and provides the appropriate compression of the septa for closure purposes. A catch member according to one embodiment is formed of an elastic material that extends beyond a proximal opening of the occluder.

In another embodiment, the catch member is a helical spring that can stretch axially. In some embodiments, the proximal end of the catch member forms a spiral that has a diameter larger than a central passage of the occluder so that the occluder is prevented from collapsing into its delivery configuration. A recess can be provided in the passage so that the spiral is at least partially disposed in the recess. This may reduce the material exposed at the end of the device and help prevent thrombus formation.

In another embodiment of the invention, the catch member may be made from a resilient material that can be stretched. The material can be solid or tubular. The proximal end has a "T" shaped end that can extend across the diameter of the central passage of the occluder.

In another embodiment of the invention, a collapsible medical device for occluding an aperture in a body is provided. The medical device has a first configuration with a reduced profile and a second configuration with an expanded profile and is adapted to be delivered through a delivery system into a desired delivery location. The medical device has a proximal side and a distal side and an occluder portion movable between a first and a second configuration. The occluder portion includes an axial passage along the length of the collapsible medical device. The medical device further includes a catch system for holding the occluder portion in the second configuration, including a catch member adapted to be disposed in the passage such that the occluder can move from the first configuration to the second configuration. The catch member includes a catch body and a catch element at its proximal end that has a dimension that is larger than a diameter of the axial passage at the proximal end of the occluder portion and a catch length provided by the catch body is adjustable to correspond to a length of the aperture.

In another embodiment of the invention, the catch member is made of polymeric material including at least one of bioabsorbable polymeric material, shape-memory polymeric material and a biocompatible metal material.

In another embodiment of the invention, the catch element is configured to seat in a recess at the proximal end of the axial passage of the occluder portion.

In yet another embodiment of the invention, the catch element includes a flange or stick or coil configured to seat in a recess at the proximal end of the axial passage of the occluder portion and the catch body is formed of an elastic material.

In another embodiment of the invention, the catch system for holding the occluder portion in the second configuration is of an adjustable catch-length in the axial direction.

According to another aspect of the invention, a collapsible medical device for occluding an aperture in a body is provided. The medical device has a first configuration with a reduced profile and a second configuration with an expanded profile and is adapted to be delivered through a delivery system into a desired delivery location. The medical device comprises an occluder portion that is adapted to move from a reduced profile configuration to an expanded profile configuration and the occluder portion includes an axial passage along the length of the occluder portion. The medical device further includes a catch system adapted to be disposed in the passage of the occluder portion such that the occluder portion can be moved from the reduced profile configuration to the expanded profile configuration with the catch member in the passage. The medical device further includes a catch member having an adjustable axial length, so that a catch distance provided by the catch member can be adapted to a dimension of the aperture when the device is delivered to the desired delivery location, a portion of the catch member configured to secure the proximal end of the occluder portion in the expanded profile configuration.

In another embodiment of the invention, the collapsible medical device further comprises a securement system for attaching the catch member to a delivery wire and attaching the occluder portion to a delivery catheter.

In another embodiment of the invention, the catch member includes a resilient spring that may optionally include an attachment piece that is adapted to attach to a deployment tool. In such embodiments, the attachment piece may includes a generally spherical ball.

In another embodiment of the invention, the proximal end of the catch member includes a T shape element for securing a proximal end of the occluder portion in the expanded profile configuration. According to another aspect of this embodiment, the T shape element may include an attachment piece that is adapted to attach to a deployment tool. The attachment piece may be a generally spherical ball.

According to another aspect of the invention, the occluder portion is made from at least one material selected from a biocompatible metal, a bioabsorbable polymer and a shape-memory polymer.

In another embodiment of the invention, the occluder portion in the first configuration is substantially cylindrical in shape and in the second configuration includes a distal set and a proximal set of petals, circumferentially arranged and radially oriented, adapted to provide compressive force on opposite sides of the aperture.

In another embodiment of the invention, the occluder portion is constructed from a substantially cylindrical portion of material with a proximal and a distal series of axial slits, each series of axial slits arranged circumferentially.

In another embodiment of the invention, the occluder portion is constructed from a series of axially-extending filaments arranged to form a substantially cylindrical occluder portion in the first configuration.

In another embodiment of the invention, a collapsible medical device for occluding an aperture in a body and a delivery system is provided. The medical device has a first configuration as a reduced profile and a second configuration as an expanded profile and is adapted to be delivered through the delivery system into a desired delivery location. The medical device comprises an occluder portion movable between a first and a second configuration that includes an axial passage along the length of the collapsible medical device with an adjustable-length center joint capable of expanding in an axial direction. The medical device further comprises a catch system for holding the occluder portion in the second configuration, including an catch member adapted to be disposed in the passage such that the occluder can move from the first configuration to the second configuration.

In another embodiment of the invention, the adjustable-length center joint includes a series of transverse slits, arranged longitudinally and capable of deforming to enable elongation of the adjustable-length center joint.

In another embodiment of the invention, the adjustable-length center joint includes a series of transverse creases, arranged longitudinally and capable of deforming to enable elongation of the adjustable-length center joint. In another embodiment of the invention, the adjustable-length center joint includes at least one spirally oriented cut, constructed and arranged to allow flexible deformation of the adjustable-length center joint. In another embodiment of the invention, wherein the adjustable-length center joint is of a braided construction capable of a range of the axial lengths in accordance with the dimension of the aperture and position of the device with respect to the aperture.

In another aspect of the invention, the adjustable-length center joint includes a first portion and a second portion, the first portion having an first cylinder with first circumferential features on an inner surface and the second portion having a second cylinder with second circumferential features on an outer surface; the second portion capable of being controllably inserted in the first portion such that the first features of the proximal portion and the second features of the distal portion are in contact and wherein contact between the first features of the proximal portion and second features of the distal portion secures said adjustable-length center joint at a selected length. According to another aspect of the invention, the first portion and the second portion are made of a resilient material capable of flexing. The first and second portions in some embodiments use a locking tab mechanism or a ratcheting grooves mechanism.

In one embodiment of the invention, the adjustable-length center joint includes: a first substantially cylindrical portion having a flexible tab or key protruding from an outer surface of the first substantially cylindrical portion, and a second substantially cylindrical portion having an axially-oriented groove and at least one locking bay adjacent to said groove, disposed along an inner surface of the second substantially cylindrical portion. The first substantially cylindrical portion is adapted to be controllably inserted in the second substantially cylindrical portion a selected distance and secured at the selected distance by rotating the first substantially cylindrical section enabling the flexible tab to engage with a locking bay and optionally applying radial force in the first substantially cylindrical portion to hold the flexible tab in place.

In another embodiment of the invention, the adjustable-length center joint includes: a first substantially cylindrical portion having a flexible tab protruding from an outer surface of the first substantially cylindrical portion, and a second substantially cylindrical portion having at least one circumferentially-oriented groove disposed along an inner surface of the second substantially cylindrical portion, and optionally. The first substantially cylindrical portion is adapted to be controllably inserted in the second substantially cylindrical portion a selected distance and secured at the selected distance by engaging the flexible tab on at least one circumferentially-oriented groove and by optionally applying radial force in the first substantially cylindrical portion to hold the flexible tab in place. In some embodiments, the flexible tab or key is replaced with a non-flexible tab or key.

In one embodiment of the invention, the adjustable-length center joint includes a first portion of substantially cylindrical shape having directional ratcheting grooves disposed on an inner surface of the first portion, and a second portion having a lesser diameter than the diameter of the first portion, having directional teeth disposed on an outer surface of the second portion adapted to engage the angled ratcheting grooves when the second portion is controllably inserted in the first portion thereby preventing separation of the first and second portions. According to another aspect of the invention, the first portion is a proximal portion and the second portion is a distal portion. According to yet another aspect of the invention, the inner surface of the first portion and the outer surface of the second portion are further contoured to provide substantial friction when the inner surface of the first portion is brought into contact with the outer surface of the second portion.

In another embodiment of the invention, the collapsible medical device is adapted to close a septal defect including a patent foramen ovale (PFO).

These and other aspects and embodiments of the disclosure are illustrated and described below

BRIEF DESCRIPTION OF THE DRAWINGS

FIGS. 5-8 illustrate an occluder according to the present invention in a sequence between a reduced profile delivery configuration (FIG. 5) and an expanded profile deployed configuration (FIG. 8);

FIGS. 22-25 illustrate an occluder according to the present invention in a sequence between a reduced profile delivery configuration (FIG. 22) and an expanded profile deployed configuration (FIG. 25);

FIGS. 29A, 29B, 30A, 30B, 31A and 31B are detail views of alternative constructions of expandable center joints;

FIGS. 32A, 32B, 33A, 33B, 34A and 34B are detail views of other embodiments of the present invention;

FIGS. 38A and 38B are detail views of an adjustable center joint with a friction-based adjustment mechanism according to another embodiment of the invention;

FIGS. 39A and 39B are alternate views of features in a friction-based adjustment mechanism for use in an adjustable center joint occluder system; and FIGS. 40A, 40B and FIG. 41 are detail views of an occluder according to another embodiment of the invention

DETAILED DESCRIPTION OF THE ILLUSTRATED EMBODIMENTS

Figure 1:
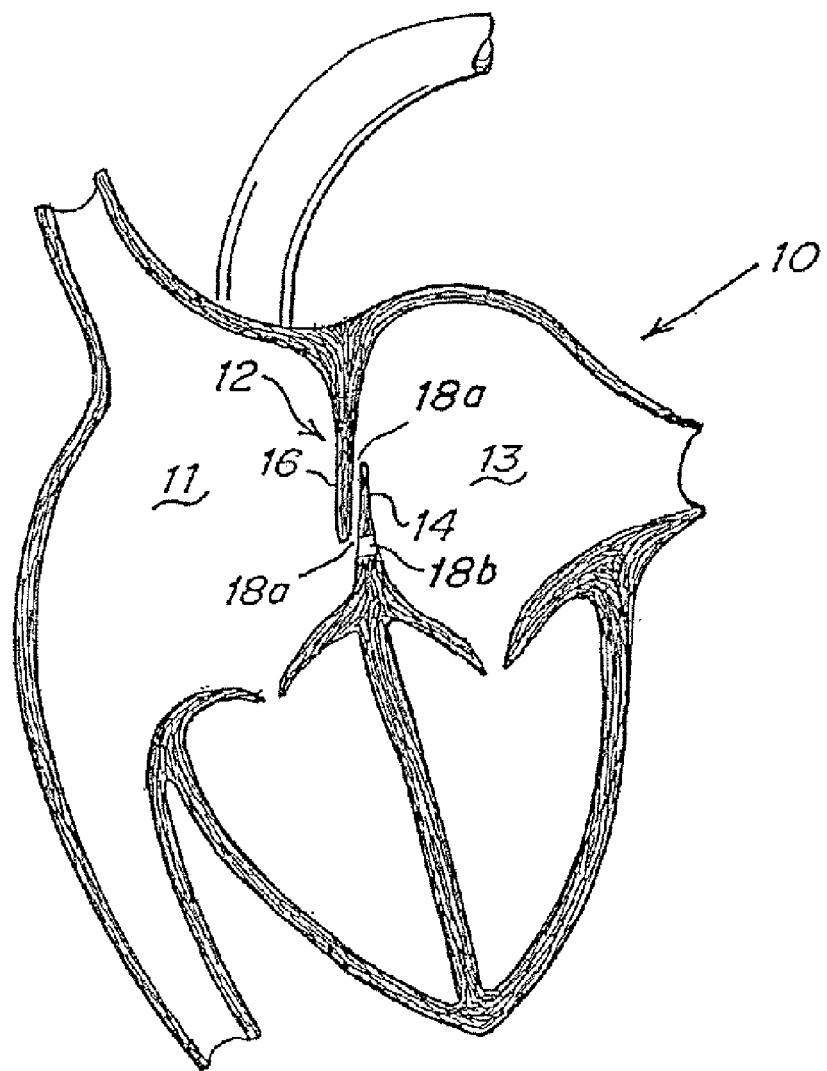
FIG. 1 is a schematic representation of a human heart including various septal defects.

Various embodiments of the present invention provide implants intended to facilitate occluding an aperture within body tissue. Aspects of the present invention include devices, delivery/retrieval systems and techniques for delivering such devices intended to occlude an aperture within body tissue. In particular and as described in detail below, the described occluder may be used for closing an ASD, ventricular septal defect (VSD) or PFO in the atrial septum of a heart. Although the embodiments are described with reference to an ASD, VSD or PFO, one skilled in the art will recognize that the devices and methods of the present invention may be used to treat other anatomical conditions. As such, the invention should not be considered limited in applicability to any particular anatomical condition. In addition, the systems and methods for delivery and retrieval, and for catching an occluder in a deployed state, which are aspects of the present invention, may also be used in connection with other types of devices besides an occluder, in particular, devices having tubular profiles.

In this application, the term "catch system" describes the portion/aspect of an implant that secures the device in the deployed configuration. The catch system may be a single piece or a group of connected or assembled pieces. In particular, the "catch member" is the portion of the catch system that engages with the occluder to hold the occluder in the deployed configuration and is described in more detail below.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has been deployed from the catheter, such as at the desired implantation location.

In this application, "catch distance" refers to the distance between the distal end and the proximal end of a catch member. The catch distance is related to the distance between the distal end and the proximal side of a deployed device, such as an occluder.

In this application, "adjustable" refers to a property of a device that can be varied, for example, according to variable anatomical geometry in individual patients, such as individual septal thickness. As will be described in greater detail below, the adjustability of the occluder device and corresponding catch member is a desirable feature. While occlusion may be constructed in a variety of sizes and dimensions, and preselected to approximately fit a particular size septal defect, an occluder device with an adjustable center-joint length permits a customized fit to the anatomical structure of the defect. An adjustable occluder has the advantage of allowing fine adjustments during implantation thereby allowing an optimal fit of the particular septal defect. In some cases an optimal fit might be achieved by angling an occlusion device to accommodate overlapping portions of septal tissue. As will be evident to one skilled in the art, optimal fit of a septal defect involves a finely tuned balance of clamping forces applied to the septa and precisely defined dimensions of an occlusion device. Thus, various embodiments of the present invention include adjustable-length occlusion devices that may be finely adjusted during implantation to achieve the optimal clamping forces.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical aperture 18a is present, blood could travel through the anatomical aperture 18a between septum primum 14 and septum secundum 16 (referred to as "the PFO tunnel"). Additionally or alternatively, blood could travel through anatomical aperture 18b, referred to as ASD.

Figure 2:
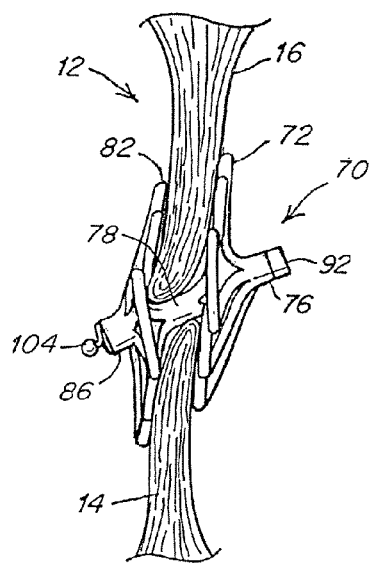
FIG. 2 illustrates a deployed occluder according to an aspect of the disclosure.

FIG. 2 illustrates an exemplary occluder with which systems and techniques disclosed herein may be used. An occluder 70, for example, is illustrated as deployed in the septum 12 of a heart. The device operates to close an aperture in the septum by covering both sides of the aperture. The reference numerals used to identify components of the described embodiment are disposed on multiple figures where the component is illustrated. The reference numerals are intended to facilitate an overall understanding of the invention and the relationship between components illustrated in different figures. The occluder 70 in FIG. 2 is shown in a human heart in a deployed configuration with a catch member 50 engaged (much of the catch member is obscured by the central tube of the occluder).

Figure 3:
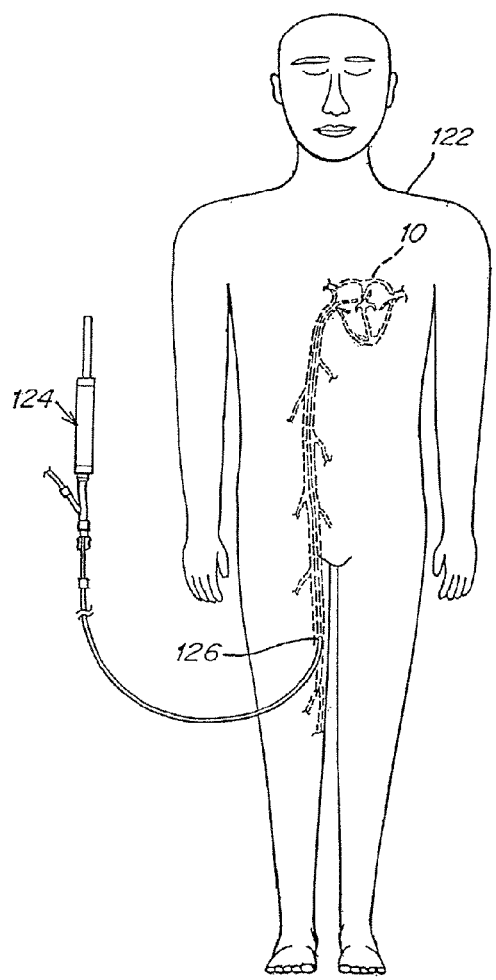
FIG. 3 illustrates introduction of the occluder in a human heart using a delivery system in accordance with an aspect of the disclosure.
Figure 4:
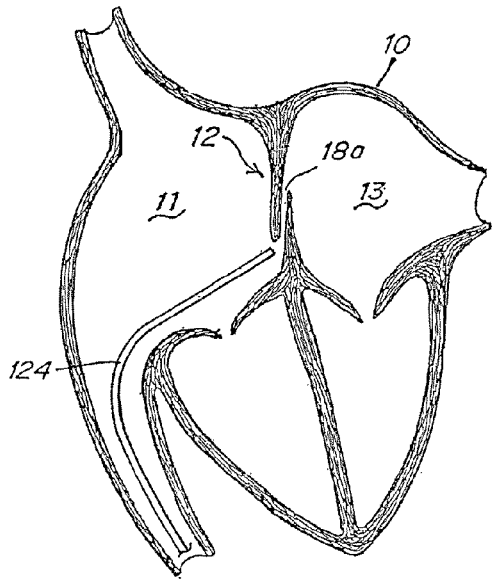
FIG. 4 illustrates a detail view of a delivery catheter in a heart with its tip approaching a PFO between the left atrium and right atrium.

FIG. 3 illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly 124 is advanced toward and into the heart 10 until the distal end is in proximity to the defect to be closed, as seen in FIG. 4.

The embodiment described below in conjunction with FIGS. 5-8 has some similarities to the device disclosed in U.S. patent application Ser. No. 10/890,784, entitled Tubular Patent Foramen Ovale (PFO) Closure Device with Catch System, filed on Jul. 14, 2004; U.S. patent application Ser. No. 11/384,635, filed Mar. 20, 2006, entitled Catch Member for PFO Occluder; U.S. patent application Ser. No. 11/235,661, entitled Occluder Device Double Securement System for Delivery/Recovery of Such Occluder Device, filed Sep. 26, 2005; and U.S. patent application Ser. No. TBD, entitled Patent Foramen Ovale (PFO) Closure Device with Linearly Elongating Petals, filed Mar. 27, 2007, all of which have the same assignee as the present application, and are incorporated herein by reference in their entirety. These incorporated applications and additional applications incorporated below describe some ways in which a device can be formed from a tube or substantially cylindrical form provided by bonding a plurality of filaments, and how to deploy and deliver such a device.

As shown in FIGS. 5-8, the occluder 70 is formed from a tube (which can be extruded or rolled) that forms distal petals 72 produced by slits 74 in the distal portion of tube according to the cutting pattern shown in FIG. 5. As shown in FIG. 6, the distal portion 20 of the tube includes eight slits 74 that form eight extended segments of the tube that form the distal loops or petals 72. As is apparent from the figures, the slits extend the entire distance of the distal portion of the tube between central tube 78 and distal end 76 so that loops of the same cross section are formed. Upon application of force $F_d$ to distal end 76, extended segments defined by slits 74 bow and twist outward to form distal petals 72 in distal side of the occluder 70. The movement of the segments during deployment is such that the segments rotate in an orthogonal plane relative to the axis of the device. Central tube 78 may be constrained during the application of force $F_d$, or any combination of forces sufficient to reduce the axial length of the tube may be applied. One end of each of distal petals 72 originates from central tube 78, while the other end originates from distal end 76 (FIGS. 6 and 7). Proximal petals 82 may be formed in proximal portion 40, as shown in FIGS. 6-8, making slits 84 between central tube 78 and proximal end 86, using the same cutting pattern described above and applying force $F_p$ or combination of forces sufficient to reduce the axial length of the tube allowing slits 84 bow and twist outward to form proximal petals 82 in proximal portion 40 of the occluder 70. One end of each of distal petals 82 originates from central tube 78, while the other end originates from proximal end 86.

The tube(s) forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated herein by reference in their entirety.

The cross-sectional shape of tube may be circular or polygonal, for example, square or hexagonal. The slits 74 and 84 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the segments could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application. In some embodiments, the tubular body of the occluder 70 is provided by aligning and selectively bonding a plurality of filaments to leave openings similar to slits 74 and 84. One of skill in the art will appreciate that references to occluder 70 and to a "tube" herein are generally applicable to an occluder 70 formed according to either technique.

The petal configuration, illustrated in FIG. 8, is the deployed configuration. The occluder 70 can be secured in the petal configuration by a catch system that holds the ends of the tube together, certain embodiments of which are described below.

The transformable design of occluder 70 enables the device to be delivered in a low profile, delivery configuration and to be converted readily, i.e., by reducing the axial length, in place to the high-profile deployed configuration. Moreover, the conversion can readily be effected by forcing distal end 76 and proximal end 86 together. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch system and deployed together as the catch element is engaged. Use of the terms distal and proximal portion 20 and 40, respectively, include the loops or other geometries and configurations that are formed on the distal and proximal sides, respectively.

Occluder 70 may be made in any one of several ways. Slits 74 and 84 may be cut such that the tube bends into its intended configuration following deployment in vivo. Specifically, slits 74 and 84 may be cut to produce segments 72 and 82 (as illustrated in FIGS. 5, 6) of a thickness that facilitates the bending and formation of loops 72 and 82 (as illustrated in FIGS. 7, 8) upon the application of forces $F_d$ and/or $F_p$ during deployment. The segments 72 and 82 that form the loops are referenced with the same reference numeral. As an alternative, or additionally, a tube formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: the tube may be only slightly preformed ex vivo such that it is predisposed to bend into its intended shape in vivo upon application of forces $F_d$ and/or $F_p$.

This particular type of occluder 70 and delivery sequences are described for purposes of illustration and explanation; of course, other types of occluders can be deployed using the deployment catch systems described herein. The catch member 50, as illustrated, is disposed in an axial passage in a radially central location (although it could be offset) in the occluder 70 and is schematically illustrated as a separate piece than the occluder 70. In a preferred embodiment, the catch member 50 may be fixed to one end of the tube that forms occluder 70. For example, a distal flange 92 may be fixed to the distal tip 39 (shown in FIG. 6 and FIG. 10) of the tube.

In general, references to "occluder 70" herein may be inclusive of catch member 50, depending on the context, for example, unless separately listed or otherwise stated. One end of tube, preferably the proximal end of the tube, is able to move with respect to the catch member 50 (and especially the catch system provided thereby) so that the distal and proximal petals 72 and 82 can move from the delivery configuration to the deployed configuration. The inside surface of the tube is able to slide over the catch member 50 so that, when the proximal end 86 of the occluder 70 rests against a proximal side (e.g. proximal side 96 or proximal stick 296) of catch member 50, the occluder 70 is secured in its deployed configuration.

The catch members described herein are for occluders in which the distance between the distal petals 72 and the proximal petals 82 in the deployed configuration is determined by the catch member and related to the catch distance, which is related to the axial length of the catch member in the permanent catch configuration. Compared to fixed-length catch systems, adjustable length catch systems of certain embodiments of the invention, described in more detail below, adjust the catch distance to the geometry of the septal defect that the accompanying device, such as an occluder, is implanted to close. By selecting the properties of materials and/or design for the adjustable length catch member, an adjustable length occlusion device can fit different patients with different defects, or be used for closing different types of defects. As such the length of the catch distance adjusts to the geometry of the septal defect to be closed, for example, by an occluder, and the adjustable length catch members provide appropriate clamping forces for tissues of different thickness, such as septa. In general, the adjustable length is provided by expandable design feature of the center joint of the occlusion device and an elastic feature of the catch member. As used herein, the terms "elastic" and "resilient" refer to a property of being stretchable, flexible or bendable from an original or rest shape, typically with a tendency to return to an original form. Generally, the materials and/or design for the elements of the catch member that allow for the adjustable catch distance are selected so that the force needed to stretch the adjustable portion of the occlusion device is greater than the force applied by the catch member to secure the occlusion device in its deployed configuration.

Figure 9A:
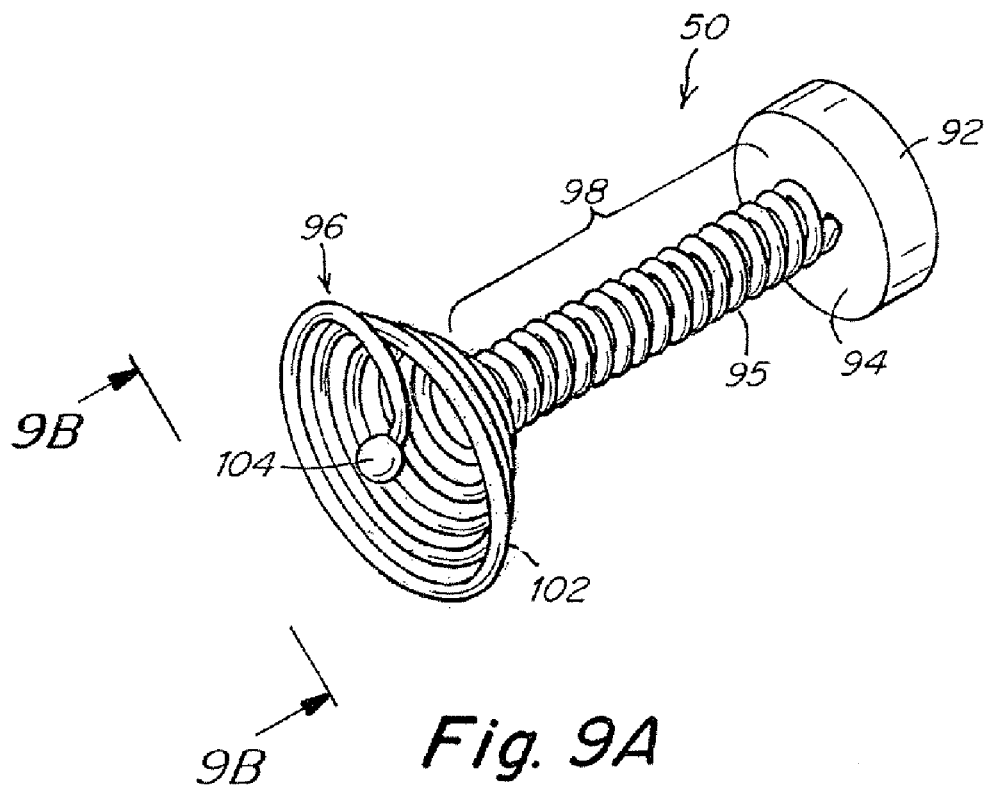
FIG. 9A is a detail view of a catch member in accordance with an embodiment of the present invention.

One embodiment of a catch system of the present invention will now be described with reference to FIGS. 9-14. FIG. 9A illustrates a catch member 50 that can be disposed in the axial passage, which may be radially centric, of the occluder 70. The catch member 50 includes a distal flange 92 that is disposed at the distal end of the occluder 70. In some embodiments, the distal flange 92 of the catch member is fixed to the occluder 70. In other embodiments, the distal flange 92 of the catch member 50 is not fixed to the occluder 70, allowing the catch member 50 to rotate with respect to the occluder 70. In one embodiment, the catch member 50 includes a distal shelf 94 that allows the distal side of the occluder 70 to move relative to the proximal side (where there is a $F_p$ or $F_d$ force applied as described in preceding paragraphs). Typically the catch member 50 has an axial length of about 5-30 mm and a diameter of approximately 0.5-3 mm. Although a circular cylinder is illustrated, a variety of cross sectional shapes can by used effectively.

According to one embodiment of the invention, catch member 50, as illustrated in FIGS. 9A-14, may be made of any metal or polymer suitable for forming a helical spring. In another embodiment, catch member 50 may be made of biocompatible metal or polymer.

In an alternative embodiment, catch member 50 may be made of shape memory material (e.g., nitinol). The thermal shape memory and/or superelastic properties of shape memory polymers and alloys permit the catch member 50 to resume and maintain its intended shape in vivo despite being distorted during the delivery and/or deployment process.

In an alternative embodiment, catch member 50 may be made of a bioabsorbable material. Exemplary bioabsorbable materials include polymers, such as polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

Figure 9B:
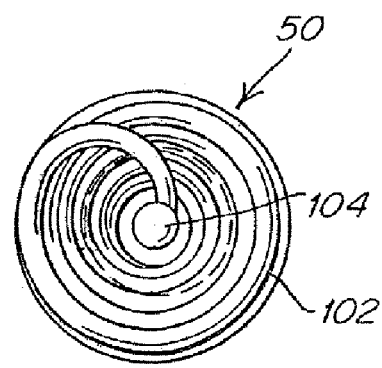
FIG. 9B is a detail end view of a catch member in accordance with an embodiment of the present invention taken along lines 9B-9B of FIG. 9A.

In a preferred embodiment, illustrated in FIGS. 9A and 9B, catch member 50 is made of elastic bioabsorbable polymer which can be stretched beyond its original length, for example to at least twice its original length. The catch member 50 includes a wire 95 that extends from the distal flange 92 to a proximal side 96 of the catch member. The wire 95 also forms a body portion 98 of the catch member. With continued reference to FIG. 9A, the body portion 98 is a helical spring configuration of wire 95 that can expand when pulled (tension applied). The proximal side 96 includes a spiral configuration 102 of wire 95. The proximal end of the catch member 50, i.e., the proximal end of the wire 95 includes a ball joint 104 so that the catch member 50 is connected to the delivery system by a clasper (not shown in FIGS. 9A and 9B) grasping the ball joint 104. FIG. 9B illustrates an end view of the catch member 50 taken along lines 9B-9B in FIG. 9A. The ball joint 104 can be centrally located in the proximal end of the catch member 50 (as illustrated) or it can be offset from the center.

FIGS. 10-14 illustrate the deployment process of the occluder 70. As illustrated in FIGS. 10-14, delivery system includes a delivery catheter 130 slidably disposed within delivery sheath (not shown), and a delivery wire 140 slidably disposed within the delivery catheter 130. Delivery wire 140 includes a wire sheath 142 that surrounds an inner wire 144 with axially projecting arms 146 at its distal end. Each of the projecting arms 146 has a cup 148 disposed on the distal end of the projecting arms 146. Although two projecting arms 146 are illustrated, according to one embodiment of the invention, three, four, five, six, or more projecting arms can be used. The cups 148 are sized and shaped to grasp the ball joint 104 of the catch member 50 and secure it when the arms 146 are disposed within the wire sheath 142. In an alternative embodiment, the connection between delivery wire 140 and the ball joint 104 of the catch member 50 can be of a ball-claw feature as disclosed in U.S. patent application Ser. No. 10/389,471, entitled Coupling System Useful in Placement of Implants, which is incorporated by reference in its entirety.

Figure 10:
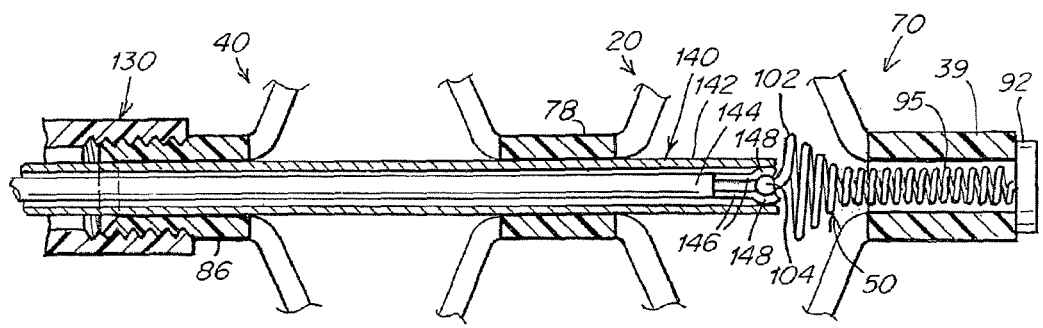
FIGS. 10-14 are detail views of a catch system and occluder according to an embodiment of the present invention during deployment.
Figure 11:
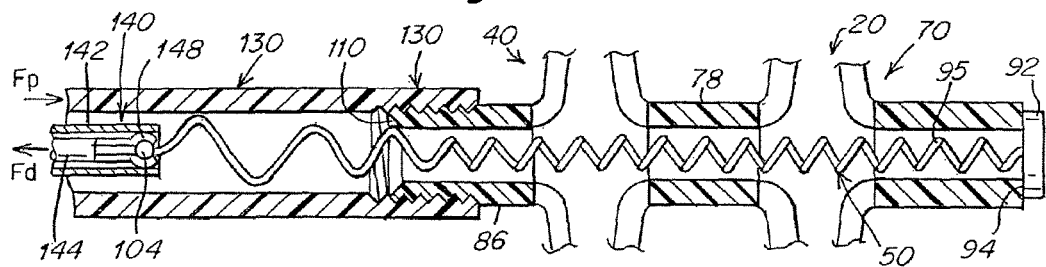

FIG. 10 is a cross sectional view of the distal end of the delivery assembly 124. According to one embodiment of the invention, the proximal portion of the occluder 70 is secured to a delivery catheter 130 with a threaded connection and the ball joint 104 is secured with cups 148 of the projecting arms 146 to the inner wire 144 of the delivery wire 140. In an alternative embodiment, the connection between delivery catheter 130 and occluder 70 could be any other suitable mechanism as described in, for example, U.S. patent application Ser. No. 11/235,661, incorporated by reference herein. As illustrated in FIG. 10, upon inserting the delivery assembly 124 to the desired location, delivery sheath (not shown) is withdrawn distally to expose the occluder 70.

Figure 12:
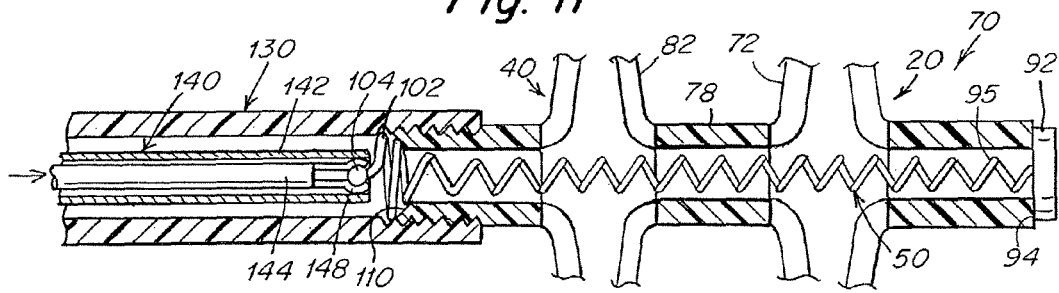

With reference to FIG. 1, a force $F_p$ is applied to the delivery catheter 130 and a force $F_d$ is applied to the delivery wire 140, such that the proximal end of the catch member 50 extends proximally in an axial direction, while the occluder 70 is maintained at its implant location. As the delivery wire 140, holding the ball joint 104, is pulled proximally, the spiral section 102 extends beyond the proximal end of the occluder 70, as illustrated in FIG. 1. The catch member can then be relaxed by stopping application of force $F_d$ on the delivery wire 140. As illustrated in FIG. 12, according to one embodiment of the invention, a conical shaped recess 110 on the proximal end of the occluder 70 could be incorporated for resting the spiral section 102 and preventing the catch member 50 from retracting further. Upon locking the occluder 70 in its deployed configuration, the spiral section 102 and distal flange 92 provide sufficient force to keep the occluder petals 72 and 82 compressed against the septum.

Figure 13:
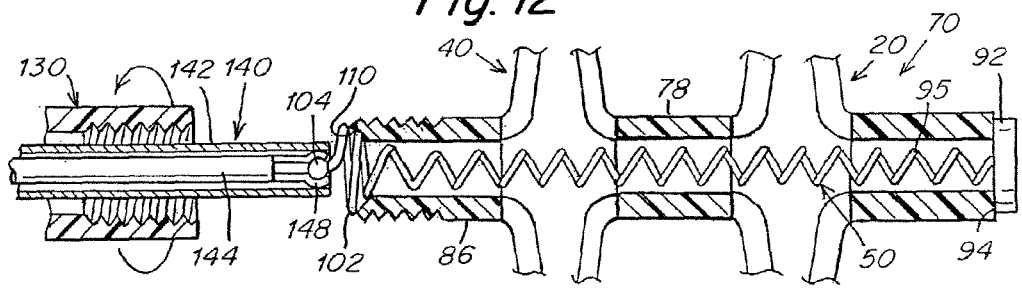
Figure 14:
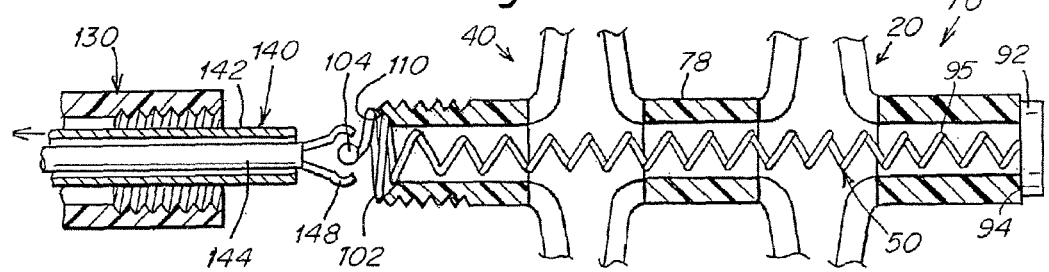

With reference to FIG. 13, the delivery catheter 130 is disconnected from the occluder 70 by disengaging the threaded connection between the delivery catheter 130 and the proximal end of the occluder 70, and retracting the delivery catheter 130 proximally. At this point, the deployment of the occluder 70 can be assessed and if needed, occluder 70 can be retrieved. Upon satisfaction with the deployment, occluder 70 can be released. According to one embodiment of the invention, illustrated in FIG. 14, the release is effected by withdrawing the wire sheath 142, which releases the ball joint 104 from the cups 148 of the projecting arms 146. The delivery assembly 124 can then be withdrawn in the direction indicated by the arrow.

When the occluder 70 is in a deployed configuration, the body portion 98 of the catch member 50 can stretch in response to the pressure exerted on the petals by the septa, which is a function of the thickness of the septa between the distal petals 72 and the proximal petals 82 (shown, e.g., in FIG. 8). For example, a thicker septa will exert a larger force on the petals 72 and 82, causing the body portion 98 of the catch member 50 to stretch more than a thinner septa, which will exert a smaller force on the petals. The axial length of the catch member 50 can therefore be adjusted and the occluder 70 can be adapted to the anatomy of individual defects during deployment.

In one embodiment, the occluder 70 can be retrieved by reversing the sequence of steps illustrated in FIGS. 10-14. For example, the inner wire 144 can be advanced distally to allow cups 148 to enclose the ball joint 104 of the catch member 50. While holding the inner wire 144 in place, the wire sheath 142 is advanced distally to cause arms 146 to close and cups 148 to grasp the ball joint 104, thereby securing the catch member 50 to the delivery wire 140. While holding the delivery wire 140 in place, the distal end of the delivery catheter 130 is advanced distally and threaded onto the proximal portion of the occluder 70, thereby securing the occluder 70 to the delivery catheter 130. While holding the delivery catheter 130 steady, the delivery wire 140 is first pulled proximally to elongate the catch member 50 and then released, which causes the catch member 50 to slide into the central passage of the occluder 70, thereby releasing the catch, as illustrated in FIG. 10. The occluder 70 can then be collapsed into its low profile configuration by advancing the delivery sheath distally or by withdrawing the delivery wire 140 and the delivery catheter 130 proximally. The occluder 70 can then be re-deployed, or if desired, withdrawn together with the delivery assembly 124 from the patient's body.

Figure 15:
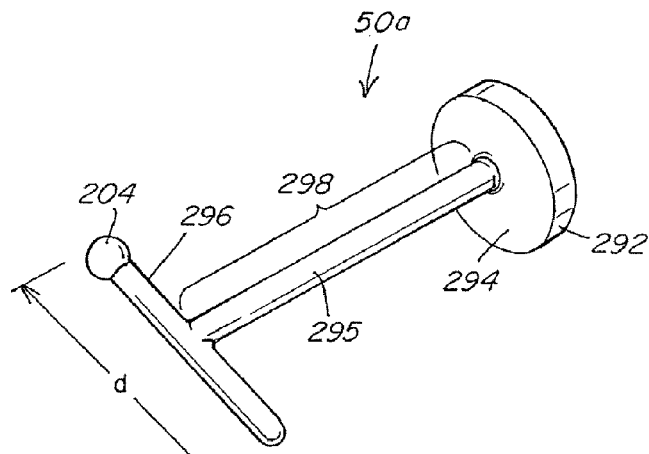
FIG. 15 is a detail view of a catch member in accordance with another embodiment of the present invention.

FIGS. 15-20 illustrate another embodiment of the present invention. FIG. 15 illustrates a catch member 50a that is disposed in the central portion of the occluder 70. The catch member 50a includes a distal flange 292 that is disposed at the distal end of the occluder 70. In some embodiments, the distal flange 292 of the catch member is fixed to the occluder 70. In other embodiments, the distal flange 292 of the catch member 50a is not fixed to the occluder 70, allowing the catch member 50a to rotate with respect to the occluder 70. In one embodiment, the catch member 50 includes a distal shelf 294 that allows the distal side of the occluder 70 to move relative to the proximal side (where there is a $F_p$ or $F_d$ force applied as described in preceding paragraphs). Typically, the catch member 50a has an axial length of about –5-30 mm and a diameter of approximately 0.5-3 mm. Although a circular cylinder is illustrated, a variety of cross-sectional shapes can by used effectively.

With continuous reference to FIG. 15, according to one embodiment of the invention, the proximal end of catch member 50a includes a proximal stick 296 and a ball joint 204 at one end of the stick so that the catch member 50a is connected to the delivery system by a clasper (not shown in FIG. 15) grasping the ball joint 204. The proximal and distal ends of the catch member 50a can be formed of a relatively rigid material, while the middle portion of the catch member 50a can be made of a more elastic material. According to one embodiment of the invention, the ball joint 204 is at one end of the proximal stick 296 as illustrated in FIG. 15.

According to one embodiment of the invention, catch member 50a, as illustrated in FIGS. 15-20, may be made of any metal or polymer with elastic property. In another embodiment, catch member 50a may be made of biocompatible metal or polymer.

In one embodiment, catch member 50a may be made of shape memory material (e.g., nitinol). The thermal shape memory and/or superelastic properties of shape memory polymers and alloys permit the catch member 50a to resume and maintain its intended shape in vivo despite being distorted during the delivery and/or deployment process.

In one embodiment, catch member 50a may be made of a bioabsorbable material. Exemplary bioabsorbable materials include polymers, such as polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

In a preferred embodiment, illustrated in FIG. 15, at least a portion of catch member 50a is made of elastic bioabsorbable polymer which can be stretched beyond its original length, for example to at least twice its original length. The catch member 50a includes a middle portion 295 that extends from the distal flange 292 to a proximal stick 296 of the catch member 50a. With continued reference to FIG. 15, the middle portion 295 of the catch member 50a can expand when pulled (tension applied). In the embodiment illustrated in FIG. 15, the proximal stick 296 is perpendicular to the middle portion 295. At least one end of the proximal stick 296 comprises a ball joint 204 so that the catch member 50a is connected to the delivery system by a clasper (not shown in FIG. 15) grasping the ball joint 204. The ball joint 204 can be located at the end of the proximal stick 296 (as illustrated), or it can be anywhere between an end and the junction of the proximal stick 296 and the middle portion 295.

FIGS. 16-20 illustrate the deployment process of the occluder 70. As illustrated in FIGS. 16-20, delivery system includes a delivery sheath (not shown), a delivery catheter 130 slidably disposed within delivery sheath (not shown), and a delivery wire 140 slidably disposed within the delivery catheter 130. Delivery wire 140 includes a wire sheath 142 that surrounds an inner wire 144 with axially projecting arms 146 at its distal end. Each of the projecting arms 146 has a cup 148 disposed on the distal end of the projecting arms 146. Although two projecting arms 146 are illustrated, according to one embodiment of the invention, three, four, five, six, or more projecting arms can be used. The cups 148 are sized and shaped to grasp the ball joint 204 of the catch member 50a and secure it when the arms 146 are disposed within the wire sheath 142. In an alternative embodiment, the connection between delivery wire 140 and the ball joint 204 of the catch member 50 can be of a ball-claw feature as disclosed in U.S. patent application Ser. No. 10/389,471, entitled Coupling System Useful in Placement of Implants, which is incorporated by reference in its entirety above.

Figure 16:
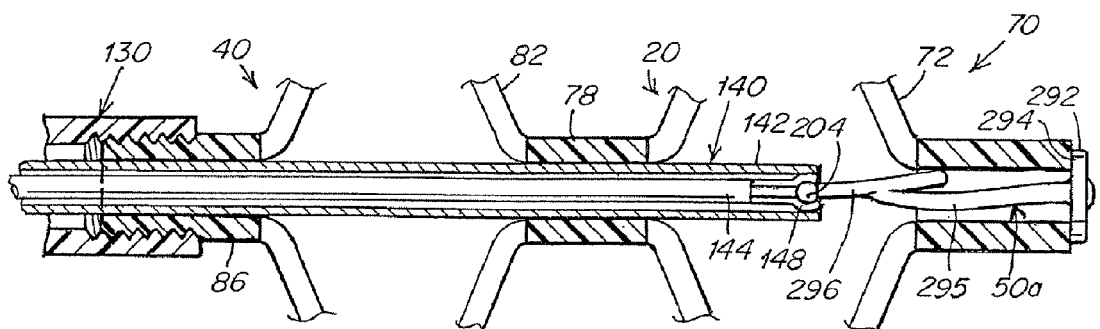
FIGS. 16-20 are cross-sectional side views of the catch system according to another embodiment of the present invention during deployment.

FIG. 16 is a cross-sectional view of the distal end of the delivery assembly 124. According to one embodiment of the invention, the proximal portion of the occluder 70 is secured to a delivery catheter 130 with a threaded connection and the ball joint 204 is secured with cups 148 of the projecting arms 146 to the inner wire 144 of the delivery wire 140. As illustrated in FIG. 16, upon inserting the delivery assembly 124 to the desired location, delivery sheath (not shown) is withdrawn distally to expose the occluder 70. In an alternative embodiment, connection between delivery catheter 130 and occluder 70 could be any other suitable mechanism as described in, for example, U.S. patent application Ser. No. 11/235,661, incorporated by reference herein. As illustrated in FIG. 16, upon inserting the delivery assembly 124 to the desired location, delivery sheath (not shown) is withdrawn distally to expose the occluder 70.

Figure 17:
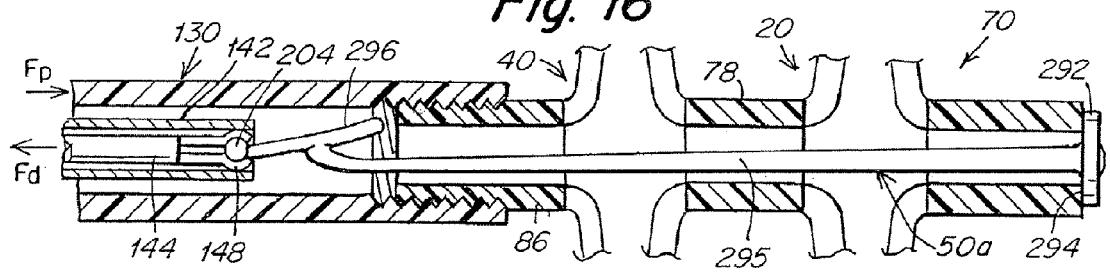
Figure 18:
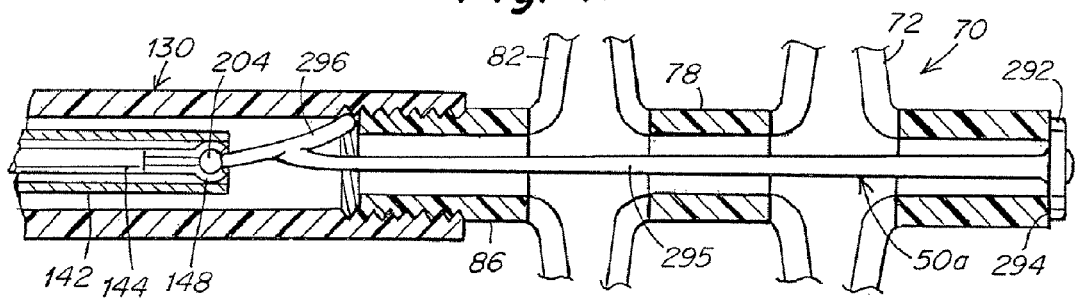

With reference to FIG. 17, a force $F_p$ is applied to the delivery catheter 130 and a force $F_d$ is applied to the delivery wire 140 such that the proximal end of the catch member 50a extends proximally in an axial direction while the occluder 70 is maintained at its implant location. As the delivery wire 140, holding the ball joint 204, is pulled proximally, the proximal stick 296 extends sufficiently beyond the proximal end of the occluder 70, as illustrated in FIG. 17. The catch member can then be relaxed stopping application of force $F_d$ on the delivery wire 140. As illustrated in FIG. 18, the proximal stick 296 has a greater dimension than the inner diameter of the proximal section of the occluder 70, thus preventing the catch member 50a from retracting further. Upon locking the occluder 70 in its deployed configuration, the proximal stick 296 and distal flange 292 provide sufficient force to keep the occluder petals 72 and 82 compressed against the septum.

Figure 19:
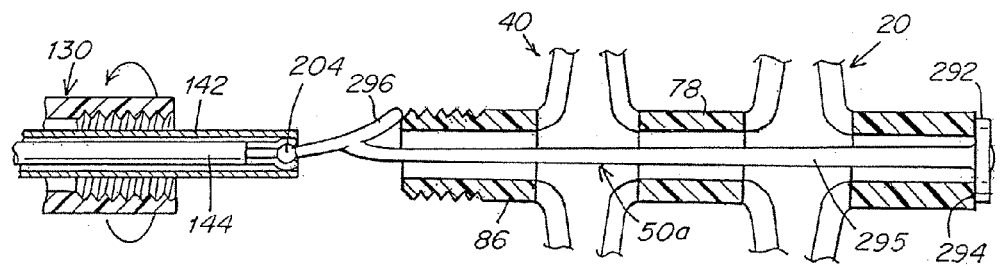
Figure 20:
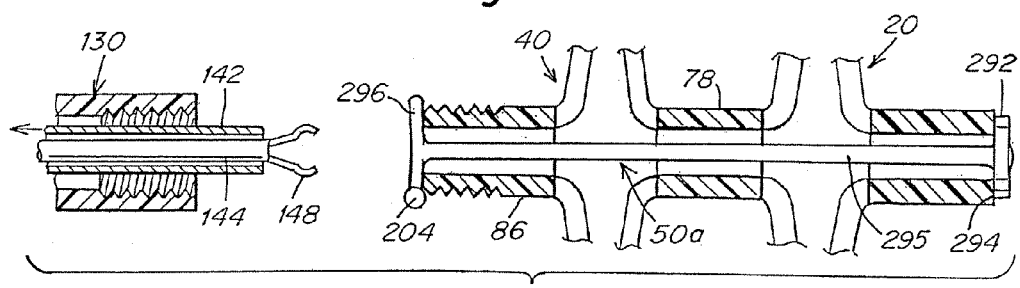

With reference to FIG. 19, the delivery catheter 130 is separated from the occluder 70 by disengaging the threaded connection between the delivery catheter 130 and the proximal end of the occluder 70, and retracting the delivery catheter 130 proximally. At this point, the deployment of the occluder 70 can be assessed and, if needed, occluder 70 can be retrieved. Upon satisfaction with the deployment, occluder 70 can be released. According to one embodiment of the invention, as illustrated in FIG. 20, the release is effected by withdrawing the wire sheath 142, which releases the ball joint 204 from the cups 148 of the projecting arms 146. The occluder 70 is held in the deployed configuration as illustrated in FIG. 20 by the catch member 50a. Upon satisfactory deployment of the occluder 70, the delivery assembly 124 can be withdrawn in the direction indicated by the arrow.

When the occluder 70 is in a deployed configuration, the middle portion 295, or a part thereof, of the catch member 50a, can stretch in response to the pressure exerted on the petals by the septa, which is a function of the thickness of the septa between the distal petals 72 and the proximal petals 82 (shown, e.g., in FIG. 8). For example, a thicker septa will exert a larger force on the petals, causing the body portion 298 of the catch member 50a to stretch more than a thinner septa, which will exert a smaller force on the petals. The length of the catch member 50a is therefore adjustable. The occluder 70 can therefore be adapted during deployment to occlude apertures in which the septal tissue has different thicknesses.

In one embodiment, the occluder 70 can be retrieved by reversing the sequence of steps illustrated in FIGS. 16-20. For example, the inner wire 144 can be advanced distally to allow cups 148 to enclose the ball joint 204 of the catch member 50a. While holding the inner wire 144 in place, the wire sheath 142 is advanced distally to cause arms 146 to close and cups 148 to grasp the ball joint 204, thereby securing the catch member 50a to the delivery wire 140. While holding the delivery wire 140 in place, the distal end of the delivery catheter 130 is advanced distally and threaded onto the proximal portion of the occluder 70, thereby securing the occluder 70 to the delivery catheter 130. While holding the delivery catheter 130 steady, the delivery wire 140 is first pulled proximally to reduce the radial dimension of the catch member 50a by increasing the angle between the ball joint-bearing side 204 of the proximal stick 296 and the body portion 298 of the catch member 50a. The delivery wire 140 is then released, which causes the catch member 50a to slide into the central passage of the occluder 70, thereby releasing the catch, as illustrated in FIG. 16. The occluder 70 can then be collapsed into its low profile configuration by advancing the delivery sheath distally or by withdrawing the delivery wire 140 and the delivery catheter 130 proximally. The occluder 70 can then be re-deployed, or if desired, withdrawn together with the delivery assembly 124 from the patient's body.

Figure 21:
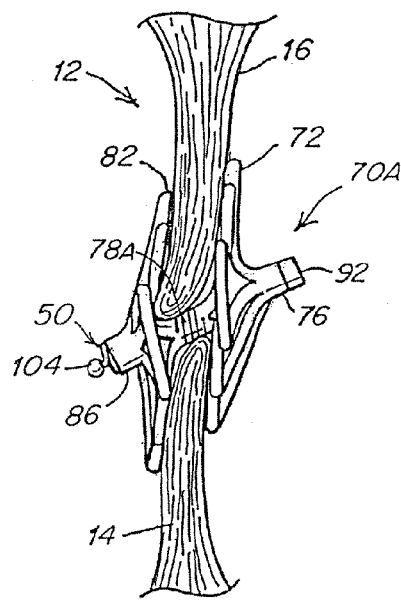
FIG. 21 illustrates a deployed occluder according to another aspect of the invention.

The adjustable length catch members described hereinabove are preferably used with occluders having a matched adjustable-length center joint. The occluder 70 described above may have the added feature of an adjustable-length center joint, which may be preferred for certain applications. FIG. 21 illustrates an exemplary occluder 70A with an adjustable-length center joint with which systems and techniques disclosed herein may be used. An adjustable-length center joint occluder 70A, for example, is illustrated as deployed in the septum 12 of a heart.

Like the occluder 70 shown in FIGS. 5-8, the occluder 70A shown in FIGS. 22-25 is formed from a tube (which can be extruded or rolled) that forms distal petals 72 produced by slits 74 in the distal portion of tube. The slits 74 in the distal portion of the tube are arranged according to the cutting pattern shown in FIG. 22. As shown in FIG. 23, the distal portion 20 of the tube includes eight slits 74 that form eight extended segments of the tube that form the loops or petals 72.

As apparent from the FIGS., the slits extend along the entire length of the distal end of the device so that the loops of the same cross section are formed. Upon application of force $F_d$ to distal tip 76, extended segments of the tube defined by slits 74 bow and twist outward to form distal petals 72 in distal side of the occluder 70A. The movement of the segments during deployment is such that the segments rotate in an orthogonal plane relative to the axis of the device. Unlike the particular embodiment of the occluder 70 shown in FIGS. 5-8, the present embodiments of the occluder include a central tube 78A with the added feature of being expandable, as described below. Expandable central tube 78A may be constrained (e.g., held within the confines of the catheter) during the application of force $F_d$. Any combination of forces sufficient to reduce the axial length of the tube may be applied, for example a combination of pulling and pushing may be used. One end of each of distal petals 72 originates from central tube 78A, while the other end originates from distal tip 76 (FIGS. 23, 24). In a manner similar to that used to form the distal petals, the proximal petals 82 may be formed in proximal side 40, as shown in FIGS. 23-25. Proximal petals 82 are formed by making slits 84 between central tube 78 and proximal end 86, using the same cutting pattern described above. Force $F_p$ can be used to create the proximal petals 82.

The petal configuration, illustrated in FIG. 25, is the deployed configuration. The occluder 70A with adjustable center joint can be secured in the petal configuration by a catch system that holds the ends of the tube together, certain embodiments of which are described herein.

The embodiments described herein, for example in conjunction with FIGS. 22-25, have some similarities to, or can be used in combination with, devices and delivery assemblies and techniques described in U.S. patent application Ser. No. 10/890,784, cited above; U.S. patent application Ser. No. 11/395,718, entitled Tubular Patent Foramen Ovale (PFO) Closure Device with Catch System, filed Mar. 31, 2006; U.S. patent application Ser. No. 11/070,027, entitled Delivery/Recovery System for Clover Leaf Septal Occluder, filed on Mar. 2, 2005; U.S. patent application Ser. No. 11/235,661, cited above; U.S. patent application Ser. No. 11/384,635, cited above; U.S. patent application Ser. No. 11/121,833, entitled Catching Mechanism for Tubular Septal Occluder, filed May 4, 2005; U.S. Patent Application No. 60/787,988, entitled Deformable Flap Catch Mechanism for Occluder Device, filed Mar. 31, 2006; U.S. Patent Application No. 60/787,987, entitled Screw Catch Mechanism for Occluder and Method of Use, filed Mar. 31, 2006; U.S. patent application Ser. No. 11/644,373, entitled Catch Members for Occluder Devices, filed Dec. 21, 2006; U.S. patent application Ser. No. TBD, entitled Patent Foramen Ovale (PFO) Closure Device with Linearly Elongating Petals, cited above; U.S. Patent Application No. 60/847,703, entitled Implant-Catheter Attachment Mechanism Using Snare and Method of Use, filed Sep. 28, 2006; all of which have the same assignee as the present application and are incorporated by reference in their entirety. Additionally, U.S. Publication US20050234509A1, entitled Center Joints for PFO Occluders, is incorporated by reference in its entirety. These incorporated documents describe some ways in which a device can be formed from a tube or substantially cylindrical form provided by bonding a plurality of filaments, and how to deliver such a device.

The transformable design of occluder 70A enables occluder 70A to be delivered in a low profile, tubular form and to be converted readily, i.e., by reducing the axial length, in place to the high-profile deployed configuration. Features of the transformable design and deployment steps are detailed above and apply to the present embodiments.

Occluder 70A may be prepared for delivery to an aperture 18 in any one of several ways, detailed above. Slits 74 and 84 may be cut such that the tube bends into its intended configuration following deployment in vivo. Specifically, slits 74 and 84 may be cut to produce segments 72 and 82 (as illustrated in FIGS. 22, 23) of a thickness that facilitates the bending and formation of loops 72 and 82 (as illustrated in FIGS. 24, 25) upon the application of forces $F_d$ and/or $F_p$ during deployment. The reference numerals 72 and 82 refer to the segments of material in a straight form and a looped form. As an alternative, or additionally, a tube formed of a shape memory material may be preformed into its intended configuration ex vivo so that it will recover its preformed shape once deployed in vivo. According to at least some embodiments, this preforming technique produces more reliable deployment and bending of occluder 70A in vivo. An intermediate approach may also be used: tube may be only slightly preformed ex vivo such that it is predisposed to bend into its intended shape in vivo upon application of forces $F_d$ and/or $F_p$.

FIG. 21, like FIG. 2, shows a deployed occluder 70A in a human heart with a catch member 50 engaged. As noted above the term "catch system" describes the portion/aspect of the implant that secures the occluder in the deployed configuration. The "catch member" is the portion of the catch system that engages with the occluder to hold the occluder in the deployed configuration. The configuration illustrated is a slightly simplified schematic view of the occluder 70A, shown in greater detail in FIGS. 22-25.

This particular type of occluder 70A and delivery sequences are described for purposes of illustration and explanation. Other types of occluders can be deployed using the deployment catch systems described herein. The catch member 50, as illustrated generally in FIGS. 24 and 25, is disposed in an axial passage, disposed in a radially central location, in the occluder 70A and is schematically illustrated as a separate piece than the occluder 70A. In one embodiment, the catch member may be attached to the distal end of the tube that forms occluder 70A as illustrated in FIG. 24. For example, a shelf that is fixed to an elongate piece of the catch member can rest against the distal tip of the occluder. This is described further and illustrated with FIGS. 28A and accompanying text.

One end of tube of the occluder 70A is able to move with respect to the catch member 50 (and especially the catch system) so that the distal and proximal petals 72 and 82 can move from the delivery configuration to the deployed configuration. The inside surface of the tube is able to slide over the catch member 50 so that, when the proximal end of the catch member rests against a proximal surface of occluder 70A, the occluder is secured in its deployed configuration. The catch member 50 is included in the catch system that includes a portion for connection to the delivery/recovery system, including, for example, a ball illustrated and described in more detail below.

Figure 26:
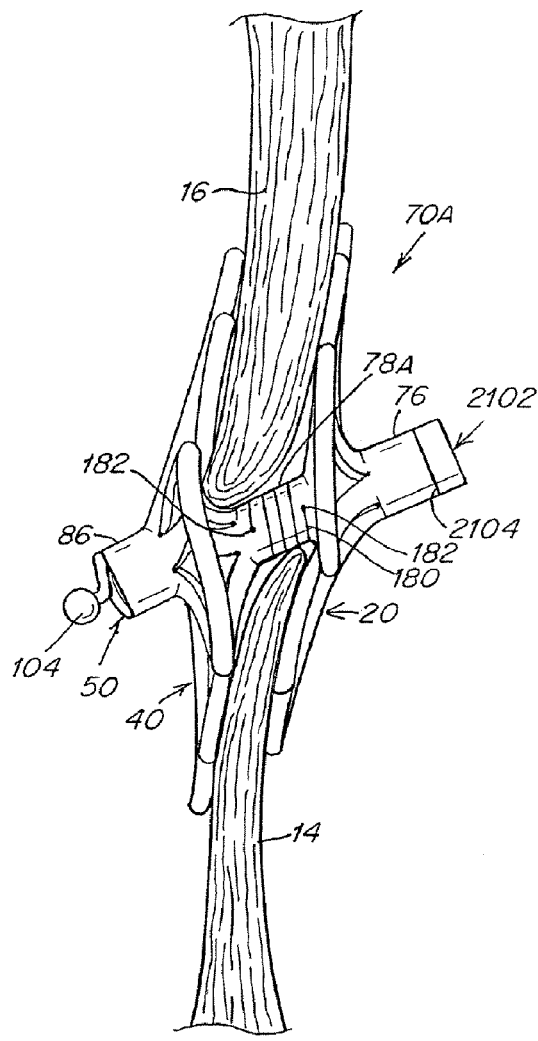
FIGS. 26-27 illustrate a detail view of an occluder with an embodiment of the present invention.

As detailed in FIG. 3, the occluder 70A is inserted in a human subject 122 using delivery assembly 124 and is secured in its deployed configuration. The expandable center joint will now be described with reference to FIGS. 26-34B. FIG. 26 illustrates the catch member 50 that is adapted to be disposed in the central portion of the occluder 70A. The catch member 50 includes a distal side 2102 that is disposed at the distal end of the occluder 70A. In some embodiments, the distal side 2102 of the catch member is fixed to the occluder. In other embodiments, the catch member is allowed to rotate with respect to the occluder. In one embodiment, the catch member includes a distal shelf 2104 that rests against the distal tip of the catch member, allowing the distal side of the occluder to be moved along with the catch member relative to the proximal side when there is a $F_p$ or $F_d$ force applied as described in preceding paragraphs. Typically the catch member has an axial length of about 15 mm and a diameter of approximately 5 mm. Although a circular cylinder is illustrated, a variety of cross sectional shapes can by used effectively.

Figure 27:
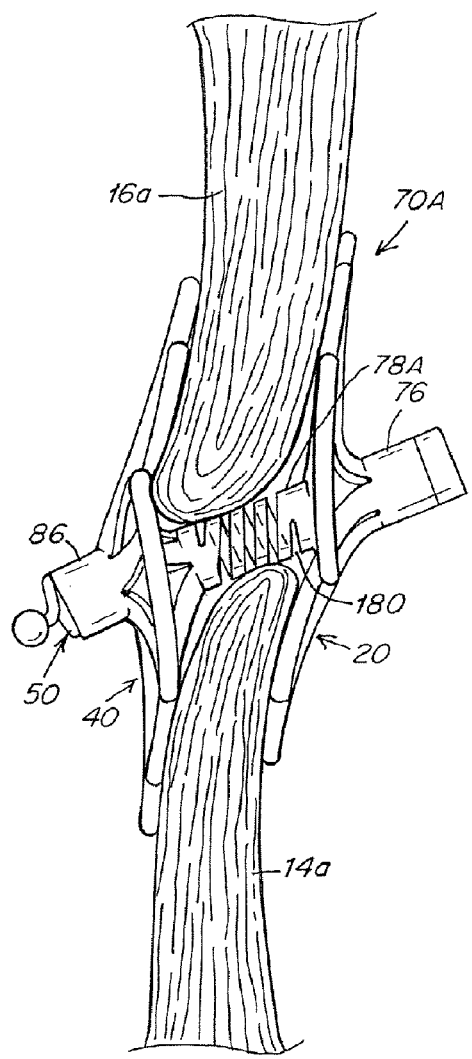

FIGS. 26-27 illustrate a detail view of an occluder 70A according to an embodiment of the present invention. As illustrated, the center joint 78A includes a spiral cut 180 that allows the joint to expand in an axial direction. The cut can be made using laser, heat, a razor, or other suitable techniques. As illustrated there are four turns in the spiral cut. More or fewer turns may be used to accomplish the axial elongation. Small holes 182 may be disposed at the end of the spiral cut to relieve stresses and reduce the possibility of tearing, splitting such that the cut would extend beyond the desired length. Occluder 70A can be used with catch members of different fixed lengths, selected based on the requirements of an individual patient. However, use with an adjustable-length catch member as described herein is preferred. Catch member 50 is designed to keep the device in the deployed configuration. Only a portion of the catch member 50 is illustrated.

FIG. 27 illustrates a thicker septum primum and secundum 14a, 16a, which causes the axial length of the device to expand when the device is deployed at the delivery site. Specifically, as illustrated, the spiral cut 180 allows the center joint to elongate so that the device can securely fit within septums of different dimensions. This allows a single occluder to be used in a number of different sized septums. Additionally, sometimes the PFO is angled, as illustrated in FIG. 1, and the length of the PFO, because of the angle, would require a center joint that is longer than if the PFO tunnel was not angled. The expandable center joint can accommodate PFO tunnels that are at a variety of angles.

Figure 28A:
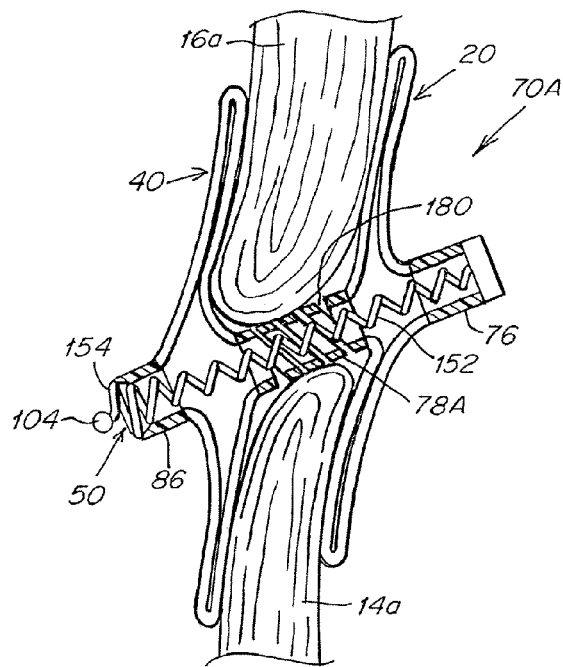
FIGS. 28A and 28B are partial cross-sectional views of a catch system deployed according to an embodiment of the present invention.
Figure 28B:
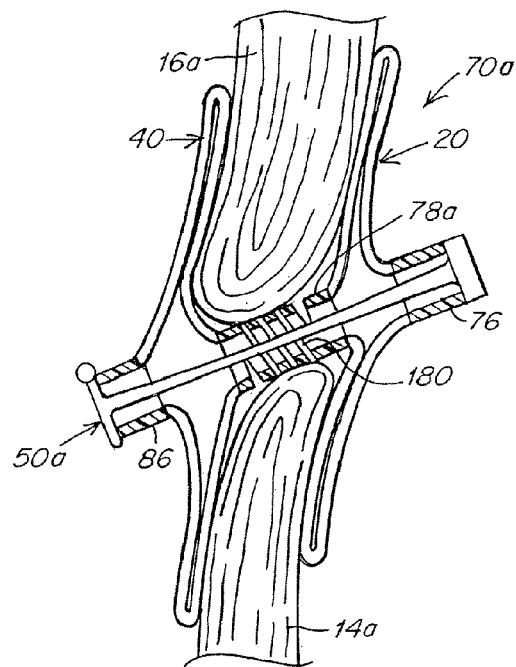

FIGS. 28A and 28B are views of a catch system deployed according to an embodiment of the present invention. In particular, FIG. 28A illustrates the catch member 50 and a coil spring 152 which applies elastic compressive force to keep the occluder in the deployed condition. An expanded spiral portion 154 at the proximal end presses against the proximal end of the occluder tube 86. A ball 104 is configured to attach to the delivery system (not shown) to allow the catch member to be pulled through the occluder (or the occluder to be pushed with respect to the catch member) to deploy the device. FIG. 28B illustrates an alternative catch member formed with elastic middle portion in the catch member that pulls the bands together.

There is a balance of forces that desirably secures the occluder in place without compressing the septum in a manner that would produce an adverse tissue reaction. If the force applied by the catch member is too great, the tissue between the occluder petals could have an adverse reaction.

For occluders with adjustable length center joints 78A, the optimum fit for each patient is achieved by either choosing a proper length catch member or by incorporating the adjustable length catch member disclosed earlier.

FIGS. 29A, 29B, 30A, 30B, 31A and 31B are detail views of alternative constructions of expandable center joints. In particular, FIGS. 29A and 29B illustrate a center joint 400 in the reduced axial dimension and the expanded axial dimension, respectively. Reference numeral 402 designates the inner lumen of the center joint. The center joint includes transverse slits arranged longitudinally, identified by reference numerals 410, 412, and 414. The slits have holes at the edge of the slits to reduce material stresses and avoid tearing or splitting when the device is expanded. When the device is pulled in the axial dimension by a force $F_p$, the slits expand and allow the center joint to elongate. Specifically, the slit 410 may form a shape illustrated in FIG. 29B. The slits 412 form a triangular shape as illustrated. The openings in the slit are designed to be in the PFO tunnel and not allow for thrombos formation. Of course more or fewer slits can be used and the length of the slits can be modified to adjust the amount of force required to elongate the center joint.

FIGS. 30A and 30B illustrate a tubular center joint 430 in the reduced axial dimension and the expanded axial dimension, respectively. The figures show a cross sectional view of a tubular, creased portion of the center joint 430. In this embodiment, the center joint is constructed of creases, e.g., 442, 444 and 446 that form angles A, B and C. When an axial force $F_p$ is applied to the center joint 430, the creases 442, 444, and 446 unfold and the angles A, B and C increase and the length of the center joint expands. The distance between the creases can be increased or decreased and the number of creases can be varied. Although illustrated such that the creases are in a zig-zag orientation (that is, the vertex of the top creases matches the vertex of the bottom creases), an alternate embodiment uses a crease alignment in which the vertex of the top matches the nadir of the bottom.

FIGS. 31A and 31B illustrate a center joint 460 in the reduced axial dimension and the expanded axial dimension, respectively. Similar to the creases in the embodiment disclosed in FIGS. 30A and 30B, the embodiment has smooth ridges, e.g., 472, 474 and 476. Upon the application of $F_p$, the ridges allow the center joint to elongate as illustrated in FIG. 31B.

In an alternate configuration, the center joint is of a braided construction such that the braids allow for variation of the axial dimension of the center joint, based on the thickness of the septum and the angle of the PFO tube.

FIGS. 32-41 illustrate a general telescoping center joint design with different detail embodiments for the occluders where the center joint can be adjusted according to the individual anatomical structure of the septal defect. Specifically, these embodiments use a telescoping feature in the center joint that allows the center joint to axially elongate. In some of the embodiments, there is a locking mechanism that keeps the center joint in the elongate configuration. One of skill in the art will appreciate that in some embodiments described, the length of the center joint is self-adjusting. Whereas in some embodiments described above, the length of the center joint is automatically adjusted and determined solely by the dimension of the aperture and more particularly by the thickness of the surrounding septal tissue, in some embodiments, the length of the center joint can be controllably adjusted by the clinician. One advantage of certain such embodiments is that the degree of clamping force provided by the distal and proximal sides of occluder 70A can be readily controlled. In general, according to one embodiment of the invention, a telescoping center joint includes an outer tube and an inner tube that have a telescoping interference fit. In such embodiments, the tube providing the body of the occluder is understood to refer to the generally tubular shape of the body of occluder, which here has a two-piece construction. The center joint may be made with resilient material that allows some bending and flexing. In one embodiment, the outer tube is the proximal portion of the center joint and the inner tube is the distal portion of the center joint. In an alternative embodiment, the outer tube is the distal portion of the center joint and the inner tube is the proximal portion of the center joint.

FIGS. 32A, 32B, 33A, 33B, 34A and 34B are detail views of other embodiments of the present invention. With specific reference to FIGS. 32A and 32B which show a telescoping center joint in a reduced axial length and an expanded axial length. In one embodiment, the outer tube 492 includes a circumferential inward projecting rim 496 that is adapted to fit within the circumferential groove 498 on the inner tube 492 and lock the telescoping pieces together. As a result, the center joint can be locked in an extended form illustrated in FIG. 32B. Additionally, a number of circumferential grooves can be used in the inside center joint to allow for a variable length in the axial dimension. In an alternative embodiment, the circumferential outward projecting rim 704 could be on the outer surface at the end of the inner tube while the circumferential groove 702 could be on the inner surface along the axial length of the outer tube, as illustrated in FIGS. 40-41. The circumferential grooves 702 could also be angled to be directional, as illustrated, thus permitting the two portions to slide together easily and then be locked together. According to one embodiment of the invention, the rim-groove design is not limited to what has been illustrated. One skilled in the art should realize that any suitable rim-groove design can be incorporated herein. In particular, for example, the interval between grooves could have any length that is suitable for a desired application.

FIGS. 33A and 33B illustrate a simplified telescoping design where the maximum axial length is determined but the pieces are able to slide within a range up to the maximum axial length. In particular the center joint 310 includes an outer tube 312 and an inner tube 314. The inner tube has an outwardly facing annular protrusion 316 (a square shape is illustrated but it could be any shape). The outwardly facing surface of the protrusion is fitted to slide within the inner surface 320 of the tube 312. The outer tube 310 also includes an inwardly facing annular protrusion 318 that prevents the inner tube 314 from sliding out of the outer tube 312.

FIGS. 34A and 34B are similar to the annular lock of FIGS. 32A and 32B but a threaded connection is provided instead of the annular protrusion. Specifically, a center joint 330 includes an outer tube 332 and inner tube 334 that slides within the tube. The end of the inner tube that is within the outer tube includes outwardly facing threads 338 that are adapted to be received by the inwardly facing threads 336 on the outer tube 332. When twisting force $F_t$ is applied to the center joint inner and/or outer tube the center joint locks into its elongate condition. In some embodiments in which only a portion of inner tube 334 has threads 338, the entire length of outer tube includes threads 336, except for a small end portion, such as portion 339. Similarly, in embodiments in which only an end portion of outer tube 332 has threads 336, almost the entire length of inner tube 334, except for a small end portion, has threads 338. This prevents the two halves from coming apart.

Figure 35A:
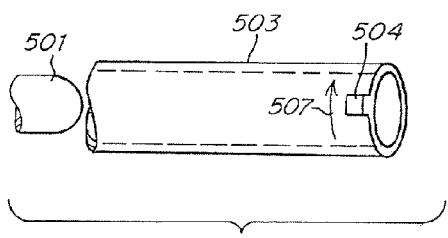
FIGS. 35A, 35B, and 35C are detail views of an adjustable center joint with a twisting tab locking mechanism, according to another embodiment of the invention.
Figure 35B:
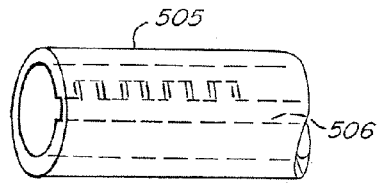
Figure 35C:
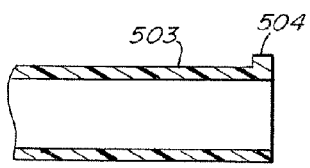

Referring now to FIG. 35, detail views of an adjustable-length center joint 78A of an occluder 70A with twisting tab-locking mechanism, according to other embodiments of the present invention, are provided. FIGS. 35A and 35C illustrate the inner tube 503 of center joint 78A. FIG. 35B illustrates the outer tube 505 of the center joint 78A. The inner tube 503 of center joint 78A depicted in FIG. 35A includes a key (or protrusion) 504 at its outer surface. In a preferred embodiment, the key 504 is at the end of the inner tube. Alternatively, the key 504 can be at any place along the length of the inner tube. FIG. 35C shows the cross-sectional view of the inner tube 503 shown from a side in which the key 504 is evident. FIG. 35B illustrates the outer tube 505, which has a length-adjustment channel 506 with locking bays on its inner surface. The locking bays are designed to fit the key 504 of the inner tube 503. The key 504 is preferably not flexible. During deployment of occluder 70A, the inner tube 503 is inserted into outer tube 505 with key 504 aligned with length adjustment channel 506. Inner tube 503 is slotted into outer tube 505 the desired distance and then secured or locked by twisting 507 inner tube 503. By twisting 507 inner tube 503, key 504 is positioned in one of the locking bays along length adjustment channel 506. Catch member 501, as illustrated in FIGS. 9 and 15, is then introduced into the inner tube 503 to secure the occluder in the deployed configuration. The catch member applies an axial compression force to the occluder thereby securing the adjustable-length center joint 78A at the desired length. The length of the center joint 78A helps control the clamping force the occluder 70A applies to the septal tissue. In an alternative embodiment, the key 504 is situated on the inside surface of the outer tube 505 while the length adjusting channel 506 and locking bay are on the outer surface of the inner tube 503.

Figure 36A:
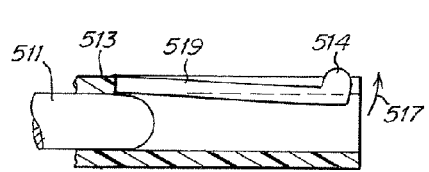
FIGS. 36A, 36B and 36C are detail views of an adjustable center joint with a sliding tab locking adjustment mechanism according to another embodiment of the invention.
Figure 36B:
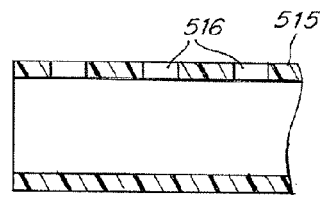
Figure 36C:
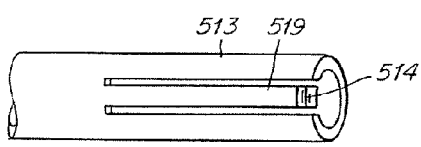
Figure 37A:
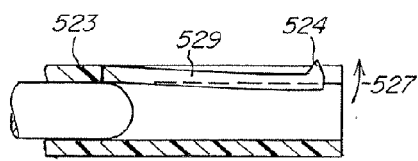
FIGS. 37A and 37B are detail views of an adjustable center joint with a continuous adjustment mechanism according to another embodiment of the invention.
Figure 37B:
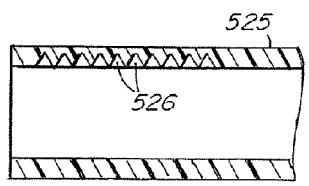

FIG. 36 shows detail views of an adjustable center joint with a sliding tab-locking mechanism according to another embodiment of the invention. Like the embodiment discussed above in FIG. 35, the present embodiment has a inner tube 513, depicted in FIG. 36A, and an outer tube 515, depicted in FIG. 36B. The inner tube 513 shown in FIG. 36A has a flexible tab 519 with a key 514 that protrudes from the surface of the flexible tab 519 which can be flexibly deformed to align the outer surface of key 514 with the outer surface of the inner tube 513. The inner tube 513 has a flexible tab 519 portion that is defined by slits provided in the end portion extending along the length of inner tube 503 as illustrated in FIG. 36C. The outer tube 515, shown in FIG. 36B, has a series of discrete locking bays 516 disposed in a portion of the surface of the outer tube 515. Adjustability of center joint 78A (of occluder 70A) is provided by sliding the inner tube 513 into the outer tube 515 the desired distance. Unlike the twisting tab-locking mechanism depicted in FIG. 35, the adjustable center joint shown in FIG. 36 is locked in position when flexible tab 519 follows motion 517 (due to the flexible nature of the design and/or the elastic nature of the material selected) causing key 514 to engage in one of the discrete locking bays 516. Catch member 511, as illustrated in FIGS. 9 and 15, is then introduced into the inner tube 513 to secure the occluder in the deployed configuration. The catch member 511 applies apply force on flexible tab 519 in the selected locking bay, causing key 514 to engage in the locking bay 516 thereby securing the adjustable-length center joint 78A at the desired length. Similar to previous embodiments, the length of the center joint 78A helps control the clamping force the occluder 70A applies to the septal tissue. In an alternative embodiment, the flexible tab 519 and key 514 are situated on the inside surface of the outer tube 515 while locking bay 516 is on the outer surface of the inner tube 503. According to one embodiment of the invention, the key-locking bay design is not limited to what has been illustrated. One skilled in the art should realize that any suitable key-locking bay can be incorporated herein, such as the one illustrated in FIG. 37.

Turning now to FIGS. 38 and 39, the adjustable center joint 78A of occluder 70A may feature a friction-based adjustment mechanism, in certain embodiments. FIG. 38A shows a cross-sectional view of outer tube 601 according to an embodiment of the invention. FIG. 38B shows a cross-sectional view of inner tube 603 according to the same embodiment of the invention. As shown in FIG. 39A, inner tube 603 may be inserted into outer tube 601, with friction at the surface 615 between the inner and outer tubes 603 and 601. FIG. 39B illustrates an exploded view of a section of the surface 615 according to one embodiment of the present invention. Surface 615 may be contoured to increase the friction between the inner and outer tubes 603 and 601. In alternate embodiments, the surface may also include positive stops or spaces whereby the inner and outer tubes 603 and 601 stop or lock in a selected position to prevent the two portions from sliding too freely or quickly. In these embodiments, the adjustable center joint 78A with the friction based adjustment mechanism shown in FIGS. 38 and 39 can include a safety mechanism to prevent the inner and outer tubes 603 and 601 from separating.

As illustrated by the embodiments described herein, the invention includes a telescoping adjustable-length center joint, which can have a variety of constructions. Any suitable construction whereby the length is adjustable and the two halves are prevented from separating.

The embodiments and techniques described here are described preferably for use with an occluder device made of a polymer and formed from a tubular or substantially cylindrical body. The occluder body or the catch mechanism as described in the embodiments above could be used with devices formed from many pieces, and including devices formed from other materials, including metals, polymers, stainless steel or nitinol.

The term "bioabsorbable," as used in the description above, is also understood to mean "bioresorbable."

In cases in which the implant is made of a polymer, it can be desirable to add an additive or coating to the material to make it radiopaque to make it more visible in a wider variety of imaging techniques.

While preferred embodiments of the present invention may specify proximal and distal ends or portions of devices, in other embodiments, it may be preferable to interchange the ends or portions. Distal and proximal should be construed as one orientation of devices in particular applications and should not be construed as restrictive.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

The illustrated embodiments and related description have been provided by way of example, and are not intended to be limiting. One of skill in the art will appreciate that variations can be made thereto without departing from the spirit and scope of the invention as indicated in the appended claims.

What is claimed is:

1. A collapsible medical device for occluding an aperture in a body, the medical device having a first configuration with a reduced profile and a second configuration with an expanded profile, the medical device being adapted to be delivered through a delivery system into a desired delivery location, the medical device comprising:
an occluder having a proximal side, a distal side, an adjustable-length center joint between the proximal side and the distal side, and an axial passage along the length of the occluder, wherein the adjustable-length center joint is configured to allow expansion of the medical device in an axial direction after deployment of the medical device in the second configuration within the aperture; and
a catch system for holding the collapsible medical device in the second configuration, the catch system including an adjustable-length catch member adapted to be disposed in the axial passage of the occluder such that the collapsible medical device can move from the first configuration to the second configuration, the catch member including a catch body having a resiliently deformable distal element for engaging the distal end of the collapsible medical device and having a dimension after deployment that is larger than a diameter of the axial passage at the distal end of the collapsible medical device and a catch element at its proximal end that has a dimension that is larger than a diameter of the axial passage at the proximal end of the collapsible medical device, wherein the catch body comprises a stretchable configuration that allows expansion of the catch member in an axial direction after deployment of the medical device within the aperture.

2. The medical device recited in claim 1, wherein the catch member is made of polymeric material including at least one of bioabsorbable polymeric material and shape-memory polymeric material.

3. The medical device recited in claim 1, wherein the catch member is made of a biocompatible metal material.

4. The medical device recited in claim 1, wherein the catch element is configured to seat in a recess at the proximal end of the axial passage of the occluder portion.

5. The medical device recited in claim 1, wherein the catch body is formed of an elastic material.

6. The medical device recited in claim 1, wherein the catch system includes a helical coil.

7. A collapsible medical device for occluding an aperture in a body, the medical device having a first configuration with a reduced profile and a second configuration with an expanded profile, the medical device being adapted to be delivered through a delivery system into a desired delivery location, the medical device comprising:
an occluder having a proximal side, a distal side, an adjustable-length center joint between the proximal side and the distal side, and an axial passage along the length of the occluder; wherein the adjustable-length center joint is configured to allow expansion of the medical device in an axial direction after deployment of the medical device in the second configuration within the aperture; and;
a catch member adapted to be disposed in the axial passage of the occluder such that the collapsible medical device can be moved from the reduced profile configuration to the expanded profile configuration, the catch member including i) a catch body having a resiliently deformable distal element for engaging the distal end of the collapsible medical device and having a dimension after deployment that is larger than a diameter of the axial passage at the distal end of the collapsible medical device, and ii) a catch element at its proximal end that has a dimension that is larger than a diameter of the axial passage at the proximal end of the collapsible medical device;
wherein the catch member has a stretchable configuration that allows expansion of the catch member in an axial direction after deployment of the medical device within the aperture, so that a catch distance provided by the catch member can be adapted to a dimension of the aperture after the collapsible medical device is delivered to the desired delivery location, a portion of the catch member configured to secure the proximal end of the occluder portion in the expanded profile configuration; and wherein an axial length of center joint in the second configuration is adjustably determined by the catch distance of the catch member.

8. The collapsible medical device recited in claim 7, further comprising a securement system for attaching the catch member to a delivery wire and attaching the collapsible medical device to a delivery catheter.

9. The collapsible medical device recited in claim 8, wherein the catch member includes a helical coil.

10. The collapsible medical device recited in claim 9, wherein the catch member includes a resilient spring.

11. The collapsible medical device recited in claim 10, wherein the resilient spring includes an attachment piece that is adapted to attach to a deployment tool.

12. The collapsible medical device recited in claim 11, wherein the attachment piece is a generally spherical ball.

13. The collapsible medical device recited in claim 8, wherein the proximal end of the catch member includes a T shape element for securing a proximal end of the occluder portion in the expanded profile configuration.

14. The collapsible medical device recited in claim 13, wherein the T shape element includes an attachment piece that is adapted to attach to a deployment tool.

15. The collapsible medical device recited in claim 14, wherein the attachment piece is a generally spherical ball.

16. The collapsible medical device recited in claim 7, wherein the collapsible medical device is made from at least one material selected from a biocompatible metal, a bioabsorbable polymer and a shape-memory polymer.

17. The collapsible medical device recited in claim 7, wherein the collapsible medical device in the first configuration is substantially cylindrical in shape and in the second configuration includes a distal set and a proximal set of petals, circumferentially arranged and radially oriented, adapted to provide clamping force on opposite sides of the aperture.

18. The collapsible medical device recited in claim 7, wherein the collapsible medical device is constructed from a substantially cylindrical portion of material with a proximal and a distal series of axial slits, each series of axial slits arranged circumferentially.

19. The collapsible medical device recited in claim 7, wherein the collapsible medical device is constructed from a series of axially-extending filaments arranged to form a substantially cylindrical occluder portion in the first configuration.

20. A collapsible medical device for occluding an aperture in a body and a delivery system, the medical device having a first configuration as a reduced profile and a second configuration as an expanded profile, the medical device being adapted to be delivered through the delivery system into a desired delivery location, the medical device comprising:
  a proximal side and a distal side for covering opposite sides of the aperture, an axial passage along the length of the collapsible medical device, and an adjustable-length center joint disposed between the proximal side and the distal side capable of expanding in an axial direction; and
  a catch system for holding the collapsible medical device in the second configuration, including an catch member adapted to be disposed in the passage such that the collapsible medical device can move from the first configuration to the second configuration, the catch member including i) a catch body having a resiliently deformable distal element for engaging the distal end of the collapsible medical device and having a dimension after deployment that is larger than a diameter of the axial passage at the distal end of the collapsible medical device, and ii) a catch element at its proximal end that has a dimension that is larger than a diameter of the axial passage at the proximal end of the collapsible medical device; and
  wherein the catch member comprises a stretchable configuration that allows axial expansion of the center joint after deployment to adjust to a length of the aperture.

21. The collapsible medical device of claim 20, wherein the collapsible medical device is composed of at least one material including biocompatible metal, bioabsorbable polymer and shape-memory polymer.

22. The collapsible medical device of claim 20, wherein a catch distance provided by the catch member can be adapted to a dimension of the aperture after the collapsible medical device is delivered to the desired delivery location.

23. The collapsible medical device of claim 20, wherein the adjustable-length center joint includes a series of transverse slits, arranged longitudinally and capable of deforming to enable elongation of the adjustable-length center joint.

24. The collapsible medical device of claim 20, wherein the adjustable-length center joint includes a series of transverse creases, arranged longitudinally and capable of deforming to enable elongation of the adjustable-length center joint.

25. The collapsible medical device of claim 20, wherein the adjustable-length center joint includes at least one spirally oriented cut, constructed and arranged to allow flexible deformation of the adjustable-length center joint.

26. The collapsible medical device of claim 20, wherein the adjustable-length center joint is of a braided construction capable of a range of the axial lengths in accordance with the dimension of the aperture and position of the device with respect to the aperture.

27. The collapsible medical device of claim 20, wherein the adjustable-length center joint includes a first portion and a second portion, the first portion having an first cylinder with first circumferential features on an inner surface and the second portion having a second cylinder with second circumferential features on an outer surface; the second portion capable of being controllably inserted in the first portion such that the first features of the proximal portion and the second features of the distal portion are in contact and wherein contact between the first features of the proximal portion and second features of the distal portion secures said adjustable-length center joint at a selected length.

28. The collapsible medical device of claim 27, wherein the first portion and the second portion are made of a resilient material capable of flexing.

29. The collapsible medical device of claim 27, wherein the: first portion has a key protruding from an outer surface; the second portion has an axially-oriented groove and at least one locking bay adjacent to said groove, disposed along an inner surface of the second portion;
  and, wherein the first portion is adapted to be secured at the selected length by rotating the first portion enabling the key to engage with one of the at least one locking bay.

30. The collapsible medical device of claim 27, wherein the: first portion has a tab protruding from an outer surface; the cylindrical portion has at least one circumferentially-oriented groove disposed along an inner surface; and wherein the first portion is adapted to be secured at the selected length by engaging the tab on one of the at least one circumferentially-oriented groove to hold the tab in place.

31. The collapsible medical device of claim 27, wherein the first portion has internal directional ratcheting grooves, and the second portion has a lesser diameter than the diameter of the first portion, and has external directional teeth adapted to engage the directional ratcheting grooves, thereby enabling adjusting the length and preventing separation of the first and second portions.

32. The collapsible medical device of claim 27, wherein the first portion is a proximal portion and the second portion is a distal portion.

33. The collapsible medical device of claim 27, wherein the inner surface of the first portion and the outer surface of the second portion are further contoured to provide substantial friction when the inner surface of the first portion is brought into contact with the outer surface of the second portion.

34. The collapsible medical device of claim 20, wherein the device is adapted to close a septal defect including a patent foramen ovale (PFO).

35. The collapsible medical device of claim 20, wherein the proximal and distal sides include a plurality of loops in the second configuration, and the loops are adapted to exert compressive force on opposite sides of the aperture.

* * * * *